(12) United States Patent
Tatum et al.

(10) Patent No.: US 8,425,396 B2
(45) Date of Patent: Apr. 23, 2013

(54) PHYSIOLOGIC PULSATILE PUMP

(76) Inventors: Tani Tatum, Bishop, CA (US); Stephen Walker, Henderson, NV (US); Bob Wilson, Bishop, CA (US)

( * ) Notice: Subject to any disclaimer, the term of this patent is extended or adjusted under 35 U.S.C. 154(b) by 198 days.

(21) Appl. No.: 12/806,918

(22) Filed: Aug. 23, 2010

(65) Prior Publication Data

US 2010/0331605 A1    Dec. 30, 2010

Related U.S. Application Data

(63) Continuation-in-part of application No. 11/788,585, filed on Apr. 20, 2007, now Pat. No. 7,785,247.

(51) Int. Cl.
*A61H 31/00* (2006.01)
(52) U.S. Cl.
USPC ............................................................ 600/16
(58) Field of Classification Search ................ 604/1–10; 422/44–45; 600/16, 151, 18; 417/43, 423.7, 417/383, 356, 412, 478; 623/3.1, 3.17, 3.24
See application file for complete search history.

(56) References Cited

U.S. PATENT DOCUMENTS 4,360,324 A    11/1982 Ohara et al.
5,044,901 A    9/1991 Fumero et al.

*Primary Examiner* — Carl H Layno
*Assistant Examiner* — Paula J Stice
(74) *Attorney, Agent, or Firm* — James E. Brunton

(57) ABSTRACT

A pulsatile blood circulating pump system for use in cardiopulmonary bypass, ventricular assist (LVAD, RVAD, BiVAD), ECMO, organ preservation, fetal cardiac bypass, cancer treatment, and areas of circulation research, which is controlled to produce blood flow that approximates physiological blood flow. The pump system includes a pulsating mechanism having a housing defining a chamber with a compressible-expandable bladder sealably mounted. A hydraulic actuator having a pressure imparting member that acts upon pressure transmissive fluid contained within the actuator chamber to generate a pulsatile pressure on the transmissive fluid, which results in pulsatile pressure being exerted on bladder to controllably vary the volume thereof. Additionally, the system includes a compact, motor that is associated with the hydraulic actuator for moving the pressure imparting member within the fluid chamber and further includes a fully programmable motion controller that controls the motor. The system includes a programmable touch-screen component to control the motion controller.

18 Claims, 19 Drawing Sheets

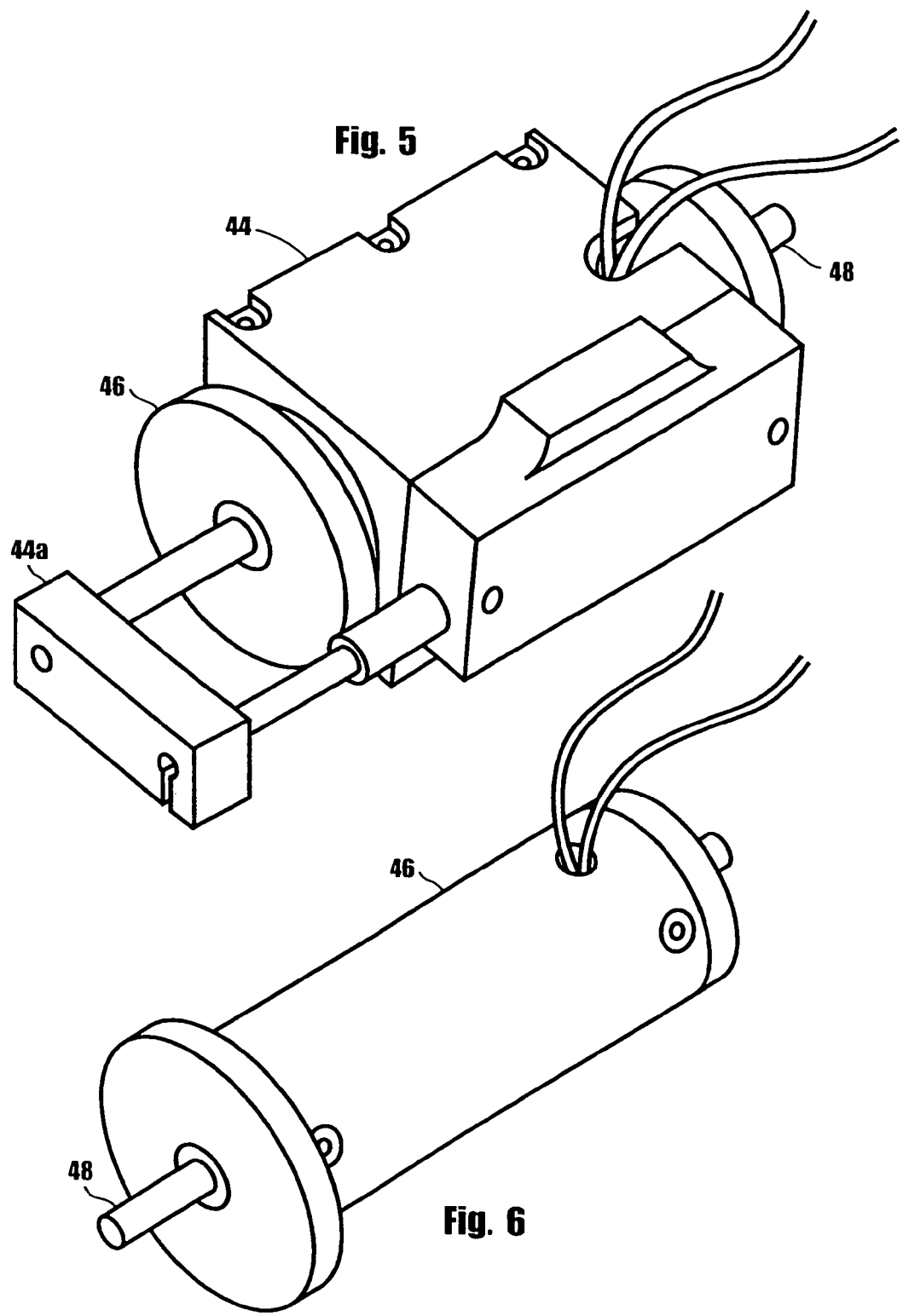

– – – "Typical" Pulse Wave Form
– ·· – ·· Stroke Volume Decreased
——— Upstroke Time Decreased
( More "Abrupt" ) Pulse Rate Increased

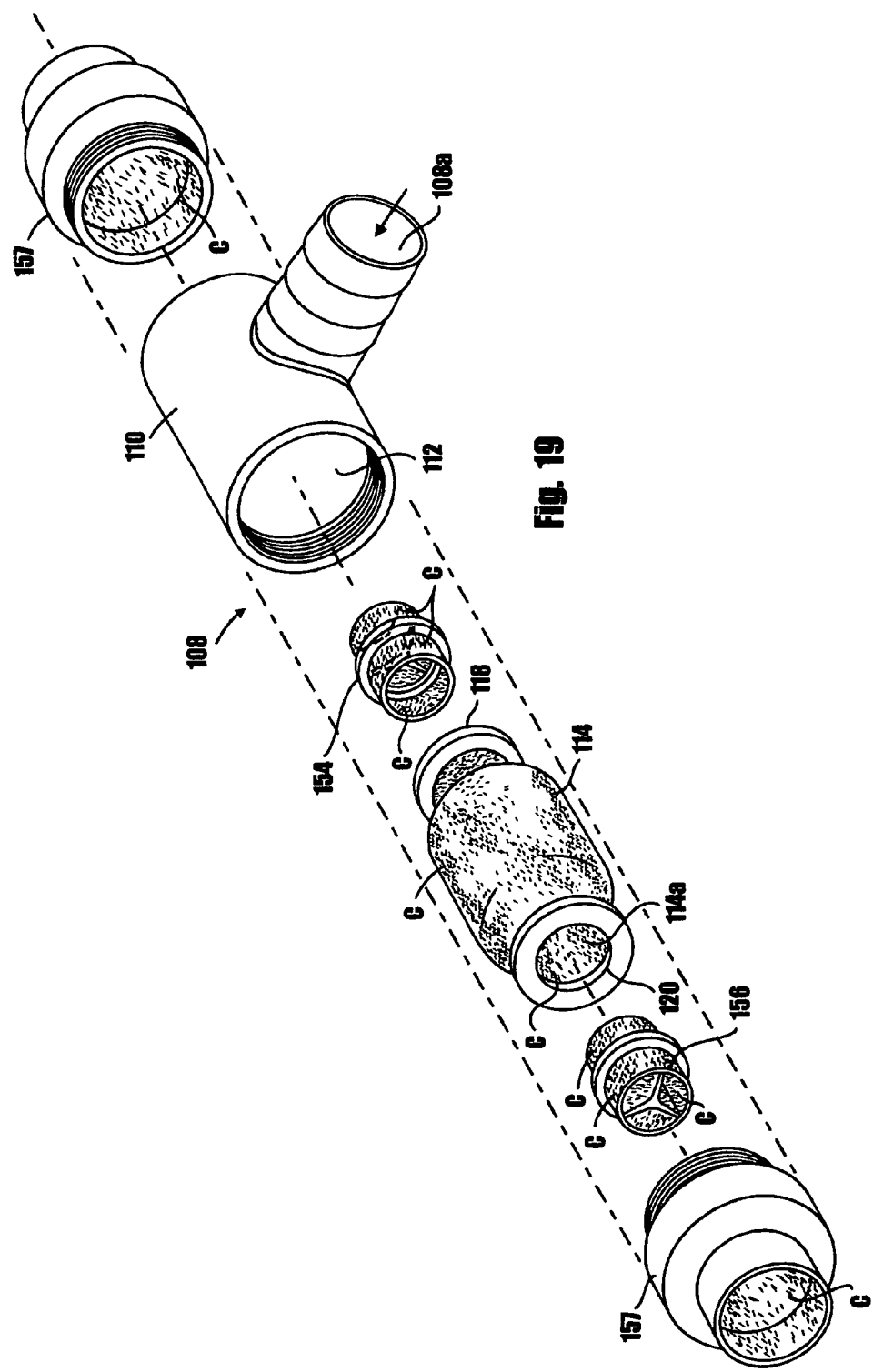

PHYSIOLOGIC PULSATILE PUMP

CROSS-REFERENCE TO RELATED APPLICATIONS

This application is a Continuation-In-Part of application U.S. Ser. No. 11/788,585 filed on Apr. 20, 2007 now U.S. Pat. No. 7,785,247.

STATEMENT REGARDING FEDERALLY SPONSORED RESEARCH OR DEVELOPMENT

Not Applicable

INCORPORATION-BY-REFERENCE OF MATERIAL SUBMITTED ON A COMPACT DISC

Not Applicable

BACKGROUND OF THE INVENTION

1. Field of the Invention

The present invention relates generally to apparatus for providing extracorporeal circulation, cardiopulmonary bypass, ventricular assist (LVAD, RVAD, BiVAD), ECMO organ preservation, fetal cardiac bypass, cancer treatment, and various areas of circulation research. More particularly, the apparatus concerns an improved physiologic pulsatile pump system that accurately duplicates blood pressure and flow patterns with no abnormal hemolysis (blood damage).

2. Description of Related Art Including Information Disclosed Under 37 CFR 1.97 and 1.98

The importance of inducing extracorporeal circulation which is as physiologic as possible has long been recognized. To Applicants' knowledge, the first and only physiologic pulsatile pump system was conceived in the mid-1950s by a heart surgeon named Selwyn Roy McCabe. During this time period, Dr. McCabe was confronted by some children in a congenital heart ward. They asked "Doctor, are we going to live or die"? Realizing that with the then present technology there was little hope for the children, he commenced work on a physiologic tricuspid valve, which then evolved to a 2-chamber physiologic pulsatile pump with a number of unique features. The doctor also envisioned that such a system could allow quality time for corrective surgery and, ultimately, prolong life support. Dr. McCabe, who was also trained in internal cardiology and physiology, felt that accurate duplication of blood pressure and flow patterns could have significant advantages to both the major vital organs and to the microcirculation.

The physiologic total life support system conceived by Dr. McCabe was successfully tested on an adult dog in Bethesda, Md. in early 1957. A neonatal/infant model, The Pediatric Pulsatile Pump, was developed in the early 70's, and a number were sold for research purposes with very successful results. The present invention comprises a technologically significantly improved version of Dr. McCabe's system.

BRIEF SUMMARY OF THE INVENTION

It is an object of the present invention to provide a pulsatile blood circulating pump system that is adapted for use in cardiopulmonary bypass, ventricular assist (LVAD, RVAD, BiVAD), ECMO, organ preservation, fetal cardiac bypass, cancer treatment, and various areas of circulation research.

Another object of the invention is to provide a pump system of the aforementioned character that can be controlled in such a way as to produce a desired blood flow that closely approximates the physiological blood flow of the patient.

Another object of the invention is to provide a pump system as described in the preceding paragraphs that includes a pulsating mechanism having a housing defining a chamber within which a compressible-expandable bladder is sealably mounted and further includes a hydraulic actuator having a pressure imparting chamber with a flexible diaphragm for generating a pulsatile pressure on the transmissive fluid. This, in turn, results in a pulsatile pressure being exerted on the bladder in a manner to controllably vary the volume thereof. Uniquely, a voice-coil actuator, including a compact, highly reliable voice-coil motor and motion controller is operably associated with the hydraulic actuator for controllably moving the pressure imparting member, here provided as a flexible diaphragm.

Another object of the invention is to provide a pump system as described in the previous paragraph that further includes a novel, fully programmable motion controller that controls the voice-coil motor.

Another object of the invention is to provide a pump system as described in the preceding paragraphs that further includes a programmable touch-screen component that functions to control the motion controller.

Another object of the invention is to provide a pump system of the character described that can be used in connection with cardiopulmonary bypass, ventricular assist (LVAD, RVAD, BiVAD), ECMO, organ preservation, fetal cardiac bypass, cancer treatment, and various areas of circulation research.

By way of summary, the foregoing objects, as well as other objects of the invention, are achieved by a physiologic pulsatile pump apparatus that includes a pulsatile flow pump that comprises a housing defining a chamber having an inlet port and a disposable, compressible-expandable bladder sealably mounted within the housing. The bladder, which has a receiving port and a delivery port, is preferably formed from an advanced antithrombogenic material. The physiologic pulsatile pump apparatus also comprises a hydraulic actuator that is connected to the housing of the pulsatile flow pump. The hydraulic actuator, which includes a fluid chamber containing a pressure transmissive fluid, has an outlet port in communication with the inlet port of the pulsatile flow pump housing. A pressure imparting member is mounted within the fluid chamber for movement therewithin in a manner to generate a pulsatile pressure on the transmissive fluid so as to, in turn, cause a pulsatile pressure to be exerted on the bladder to controllably vary the volume thereof. A voice-coil motor is operably associated with the hydraulic actuator for controllably moving the pressure imparting member within the fluid chamber. Additionally, the physiologic pulsatile pump apparatus includes a fully programmable motion controller for controlling the voice-coil motor and a programmable touch-screen component that functions to control the motion controller.

BRIEF DESCRIPTION OF SEVERAL VIEWS OF THE DRAWINGS

FIG. 5 is a generally perspective view of the voice-coil actuator sub-assembly of the apparatus shown in FIG. 2.

FIG. 6 is a generally perspective view of the voice-coil motor of the assembly shown in FIG. 5.

FIG. 19 is a generally perspective, exploded view of the pulsatile pump sub-assembly of the apparatus shown in FIG. 15.

DETAILED DESCRIPTION OF THE INVENTION

Figure 1:
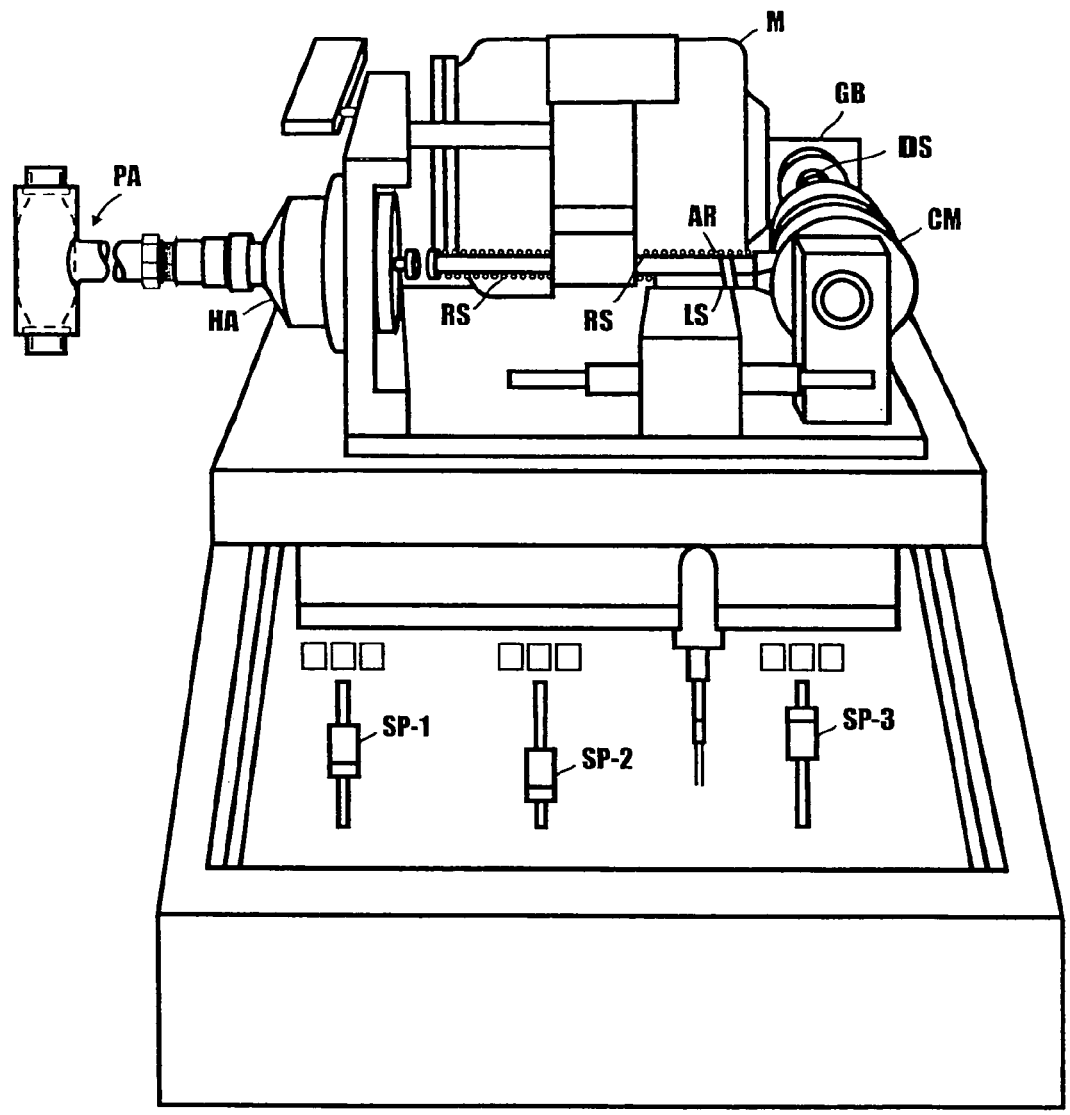
FIG. 1 is a generally perspective view of the prior art pulsatile pump apparatus developed by Dr. McCabe.
Figure 1A:
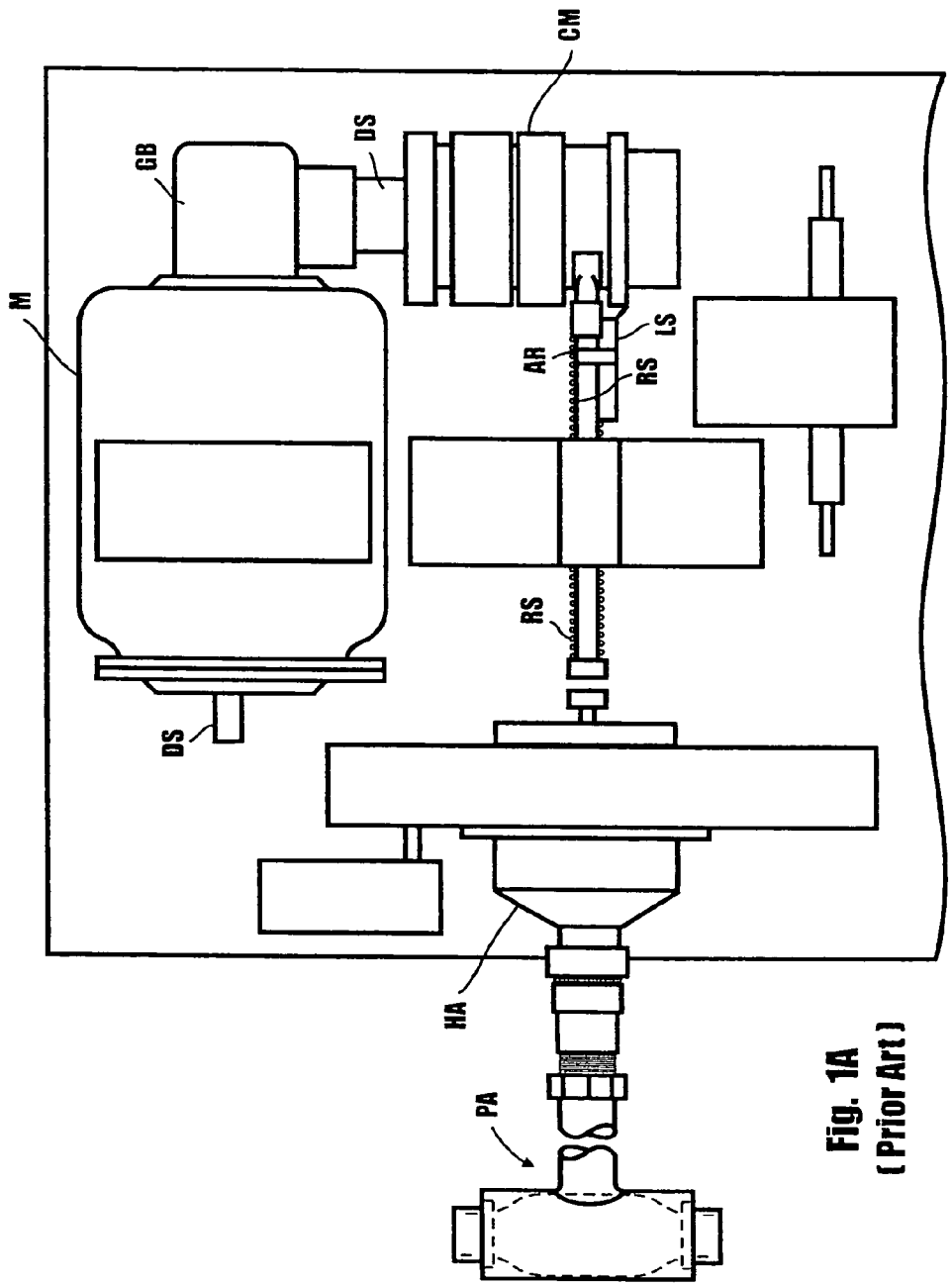
FIG. 1A is a fragmentary, top plan view of a portion of the prior art pulsatile pump apparatus developed by Dr. McCabe.
Figure 2:
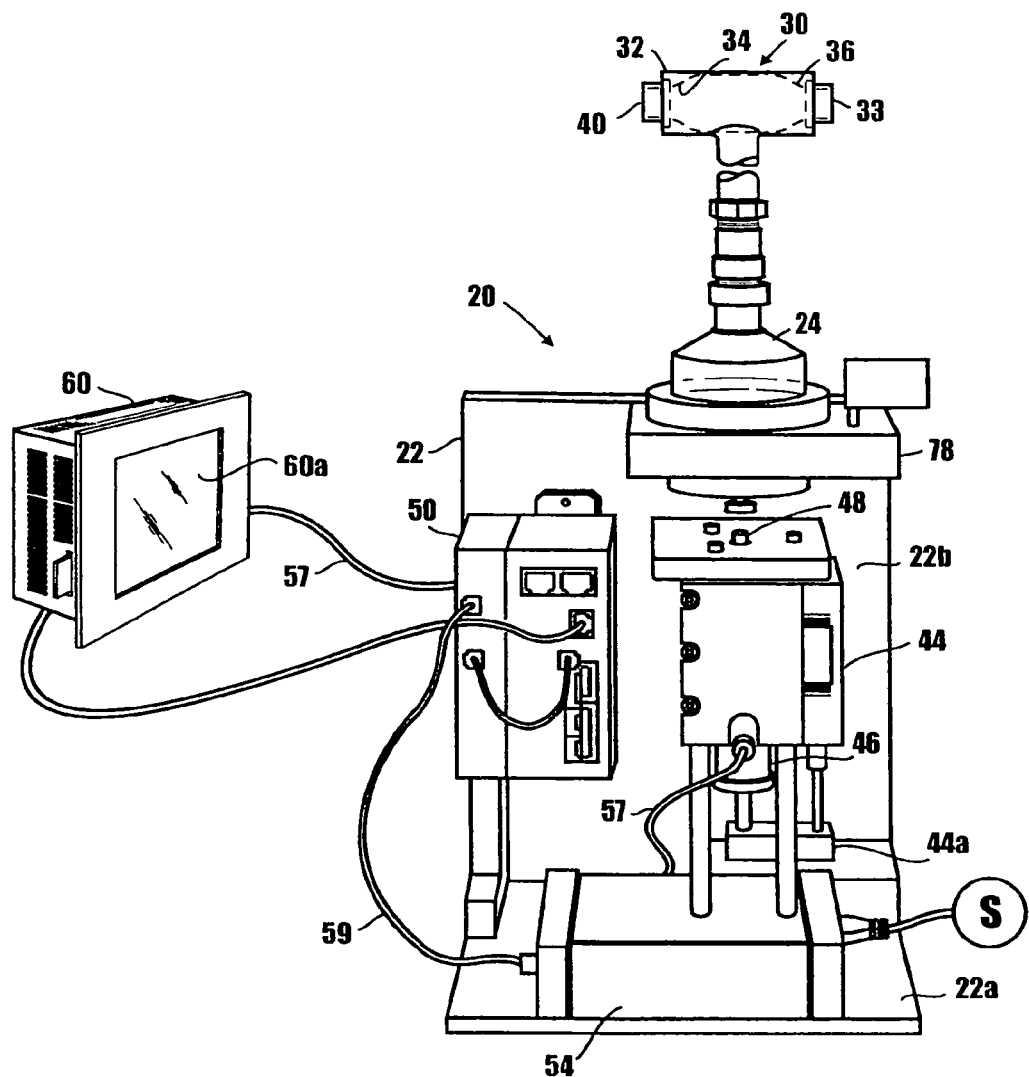
FIG. 2 is a generally perspective view of one form of the physiologic pulsatile pump system of the present invention.

Considering first the prior art system illustrated in FIG. 1 of the drawings, this system, which at the time of its development represented a substantial advance in the art, exhibited numerous technological limitations not found in the vastly improved system of the present invention shown in FIG. 2 of the drawings. For example, the prior art system was analog and, therefore, not programmable. Further, the critical system variables, including pulse rate, stroke volume and upstroke-rise time were controlled by three separate slide potentiometers "SP-1," "SP-2" and "SP-3" with light emitting diode (LED) read-outs adapted to permit individual control of each variable. In practice, the LED's were hard to read and as they started to fail, frequently caused erroneous readings to occur. Further, in the prior art system, the pulse rate control required an additional three position multiplier switch to enable it to achieve the full range. Additionally, the slide potentiometer housing of the apparatus undesirably exhibited open space to the interior electronics which could permit fluids, including blood, to reach the interior of the control housing and thereby contaminate the electronics there within.

Because of the technological limitations inherent in the prior art system, response time, position control and operational accuracy were limited, trouble-shooting was tedious and diagnostic ability was quite limited.

From a mechanical standpoint, the prior art system as illustrated in FIG. 1 of the drawings was made up of components that were quite bulky, heavy and cumbersome to use and install. The motor "M" of the apparatus, which drove the hydraulic actuator "HA" of the system via a relatively complex clutch mechanism "CM", was a 90 Volt DC motor with brushes which required periodic maintenance. The drive shaft "DS" of the motor was interconnected with a gear box "GB" having a 40:1 gear ratio. Connected to the gearbox at a 90° angle was a custom shaft "DS". Mounted on the shaft "DS" was a custom-made concentric flywheel. Attached to the flywheel was a forwardly extending actuating rod "AR", which on its forward stroke drove the actuating piston of the hydraulic actuator, which was connected to the pump assembly "PA" of the apparatus. Operably associated with the actuating rod were two sets of return springs "RS" that functioned to return the actuating piston to its starting position upon the system electronics releasing the clutch mechanism. Attached to the clutch mechanism "CM" was an adjustable limit switch assembly "LS".

Undesirably, periodic maintenance of the prior art system was required because of continuous wear on the motor brushes, the gearbox and the clutch mechanism. Additionally, the gearbox required periodic maintenance. The clutch mechanism, which was exposed to air, could get dirty, at which time it would malfunction. A dust cover was made to cover the motor/clutch mechanism. Further, the clutch mechanism exhibited a limited life expectancy and replacement of the clutch mechanism would require time-consuming and expensive factory assistance.

Figure 7:
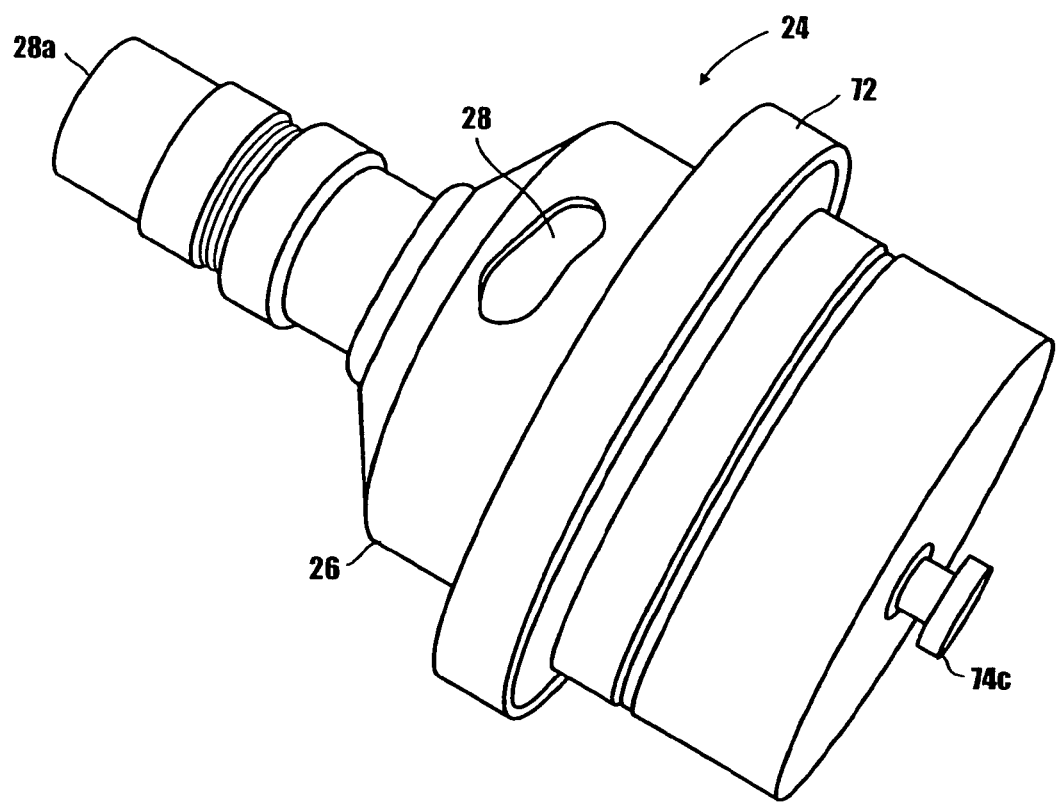
FIG. 7 is a generally perspective view of the hydraulic actuator sub-assembly of the apparatus shown in FIG. 2.
Figure 8:
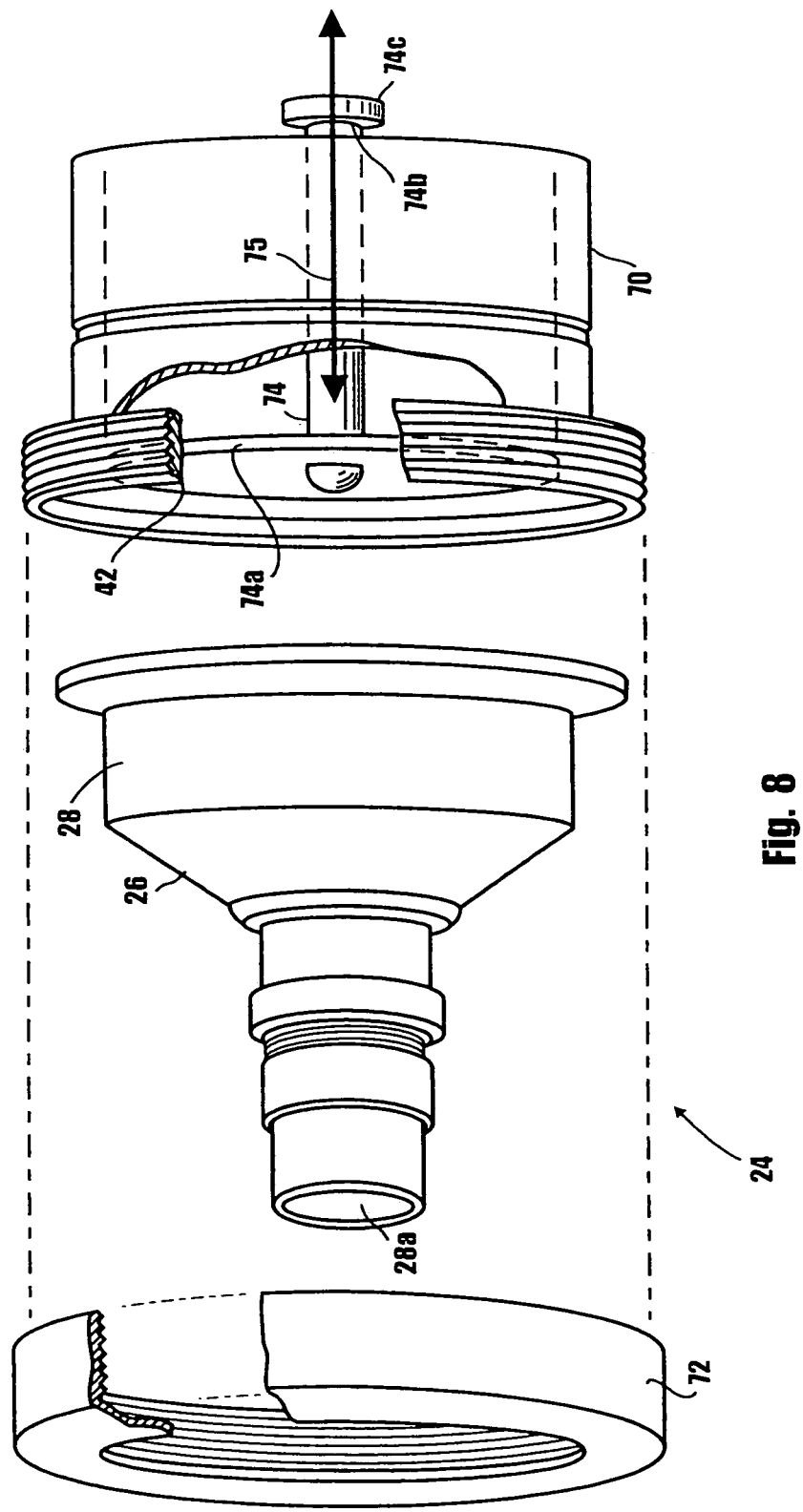
FIG. 8 is a generally perspective, exploded view of the hydraulic actuator sub-assembly shown in FIG. 7.

Referring now to FIG. 2 the drawings, one form of the physiologic pulsatile pump apparatus of the present invention is there illustrated and generally designated by the numeral 20. This apparatus, which is adapted primarily for use in cardiopulmonary bypass, ventricular assist (LVAD, RVAD, BiVAD), ECMO, organ preservation, fetal cardiac bypass, cancer treatment, and various areas of circulation research, here comprises a support assembly 22 having a base member 22a and a substantially vertical member 22b that is connected to the base member and extends there from. The voice-coil actuator motor has only one moving part, namely, a shaft moving through a bearing. These types of motors have been running in space applications for over 20 years of continuous operation, and their life expectancy is extended substantially when the motors are mounted in a vertical orientation. Connected to the vertical member 22b is a hydraulic actuator sub-assembly 24 having a housing 26 that defines a fluid chamber 28 having an outlet 28a (FIGS. 7 and 8). The function of this hydraulic actuator sub-assembly will presently be described.

Operably associated with the hydraulic actuator sub-assembly 24 is the important pulsatile flow pump 30 of the invention, which includes a fluid inlet port 30a that is in communication with outlet 28a of the hydraulic actuator sub-assembly in the manner shown in FIG. 2. As will be presently described in greater detail, pulsatile flow pump 30 in cooperation with the actuator sub-assembly 24, functions to generate a pulsatile blood flow that substantially duplicates that of the patient as recorded by a chart recorder.

Figure 9:
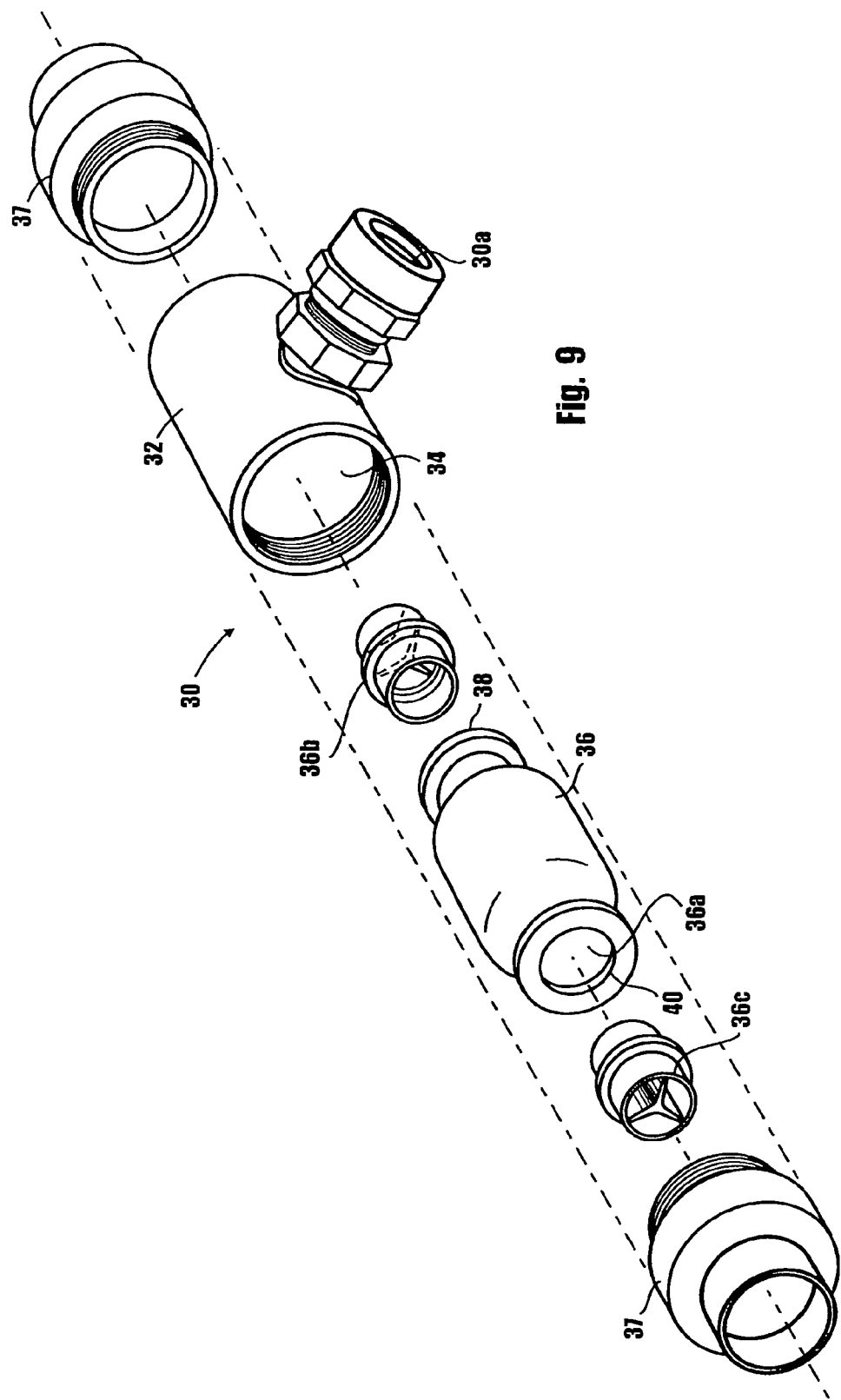
FIG. 9 is a generally perspective, exploded view of the pulsatile pump sub-assembly of the apparatus shown in FIG. 2.

As best seen by referring to FIGS. 2 and 9, mechanism 30 comprises a housing 32 defining a chamber 34 within which is mounted a disposable, compressible-expandable bladder 36 formed from an advanced, antithrobogenic, long-life material. Bladder 36 includes a bladder chamber 36a having a receiving port 38 and a delivery port 40, both of which are in communication with the patient "P" in the manner illustrated in FIG. 10.

As best seen in FIG. 8 of the drawings, sealably mounted within the fluid or actuator chamber 28 of the hydraulic actuator is an actuating member or diaphragm 42 that, during operation of the apparatus, acts upon a pressure transmissive fluid contained within the actuator chamber 28 in a manner to generate a pulsatile pressure on the transmissive fluid. As will be described in greater detail hereinafter, the pulsatile pressure generated on the transmissive fluid by the actuating member 42 results in a pulsatile pressure being exerted on bladder 36 in a manner to controllably vary the volume thereof.

As will be discussed in greater detail hereinafter, operably associated with hydraulic actuator sub-assembly 24 is a voice-coil actuator assembly 44 (FIGS. 2 and 5) that functions to controllably move the actuating member 42 of the hydraulic actuator sub-assembly within the fluid chamber 28 thereof (see FIG. 8). Voice control actuator 44 includes a supporting frame 44a that is connected to substantially vertical member 22b and strategically supports a magnetic voice-coil motor 46 having a reciprocating shaft 48 (FIGS. 5 and 6). In a manner presently to be described, during operation of the apparatus, shaft 48 controllably acts upon actuator member 42 to create the pulsating flow. Voice-coil linear actuator, or motor 46, is readily commercially available from a number of sources, but an actuator offered for sale by H2W Technologies of Valencia, Calif. under the designation NCM10-15-020 and having a stroke of approximately 0.5" (½ inch) has proven quite satisfactory for present purposes. Motor 46 has numerous advantages over the motor of the prior art apparatus illustrated in FIG. 1 of the drawings, including being considerably smaller and lighter, being substantially safer and more reliable in operation, requiring no maintenance and advantageously readily controllable in much the same manner as a conventional servo-motor. Use of the voice-coil actuator 44 in the apparatus of the present invention advantageously eliminates the dual 90°-angled shafts, the concentric fly wheel, the gearbox, the difficult-to-service electromagnetic clutch, and return springs of the previously described prior art apparatus illustrated in FIG. 1.

Figure 4:
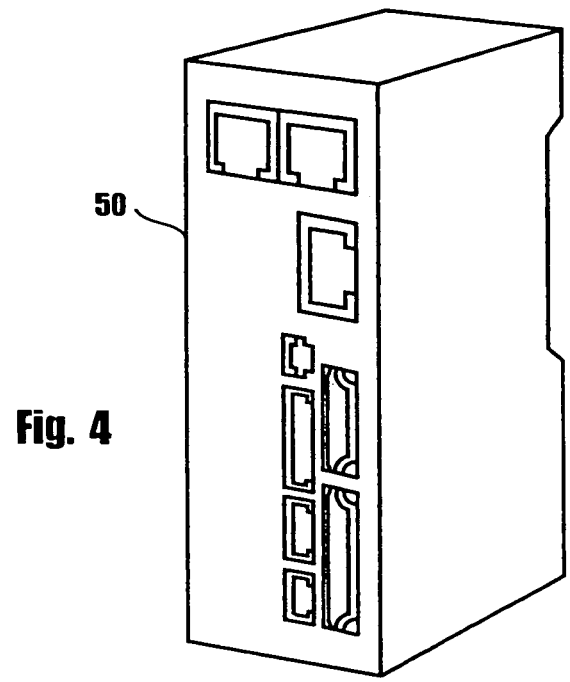
FIG. 4 is a generally perspective view of the programmable motion controller component of the apparatus shown in FIG. 2.

Also connected to vertical support member 22b of support 22 is a motion controller 50 that is operably associated with the voice-coil motor 46 for precisely controlling the motor (see FIGS. 2 and 4). Motion controller 50, which is of conventional construction, is readily available from several sources, including the Elmo USA Company of Westford, Mass. Motion controller 50, which comprises a readily programmable, state-of-the-art digital control system, provides closed-loop linear position control and utilizes RS-232 communication, which is a standard form of serial communication that is a recommended standard form of serial communication through a computer to control hardware such as the voice-coil actuator 46. Advantageously, motion controller 50 provides fast response time, accurate position control and permits remote trouble-shooting capability. Additionally, limit controls can be accurately programmed into the electronics of the controller with selected read-outs, if desired, thereby providing a high degree of safety during operation of the apparatus of the invention.

When compared to the prior art apparatus shown in FIG. 1 of the drawings, it is abundantly clear that the use of motor controller 50 in the apparatus of the present invention provides substantially greater safety, greater reliability and superior compatibility with and control over cooperating operating components, such as the hydraulic actuator driving motor, the EKG-trigger and like peripherals.

As illustrated in FIG. 2 of the drawings, to provide electrical power to the motor 46 and to the motion controller 50, a conventional power supply 54 is suitably mounted on the horizontal member 22a of the support assembly 22 and is connected to a suitable source of power "S". Power supply 54 is readily commercially available from a number of sources, including the previously identified H2W Technologies of Valencia, Calif. Suitable cabling, including cables 57 and 59, interconnect the power supply with the motor 46 and the motion controller 50.

Figure 3:
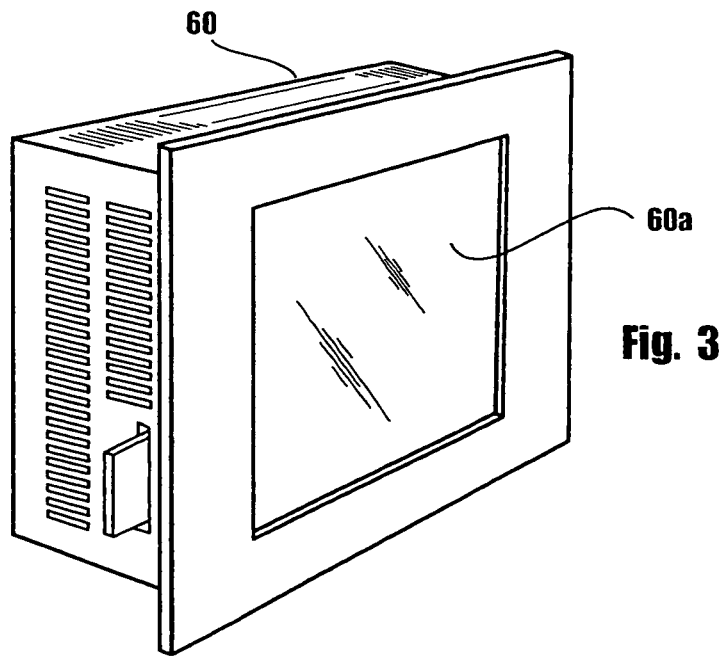
FIG. 3 is a generally perspective view of the touch-screen component of the apparatus shown in FIG. 2.

Operably associated with motion controller 50 via a connector 51 is a touch-screen unit 60 (FIGS. 2 and 3). Touch-screen unit 60, which includes desired color read-outs, is readily commercially available from a number of sources including the ESA Technology Company of Windsor, Calif. Touch-screen unit 60 here comprises a state-of-the-art touch-terminal that greatly simplifies the operation and control of the interactive components of the apparatus of the present invention. The touch-screen unit includes a rugged touch-screen 60a upon which graphic images in various formats, such as those illustrated in FIGS. 12 and 13 can be imported. During operation of the apparatus of the invention, the read-outs on the touch-screen 60a that are easy to see can be quickly and precisely changed on-the-fly and, in a manner presently to be discussed, automatically activate with an EKG signal. When compared with the apparatus of the prior art as illustrated in FIG. 1 of the drawings, the apparatus of the present invention that includes the cooperatively associated motion controller 50 and the touch-screen unit 60, permits significantly greater control of pulse rate, stroke volume, and upstroke-rise time as well as providing much more precise resolution.

Figure 11:
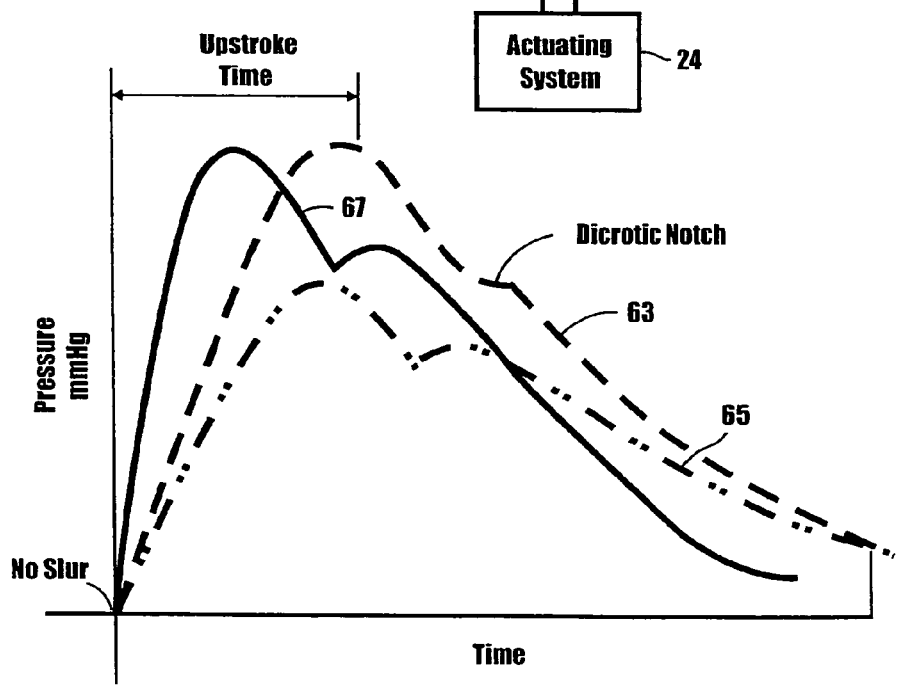
FIG. 11 is a generally diagrammatic view illustrating a set of typical blood-pressure curves.

The apparatus of the invention as described in the preceding paragraphs is designed to accurately duplicate a blood pressure curve by independently varying pulse rate, that is the number of beats per minute; stroke volume, that is the volume of blood pumped on each beat and upstroke-rise time, that is the duration of time from the start to peak pressure at the top of the curve on each beat. In a potential clinical application, as for example, a cardiopulmonary bypass procedure or an organ preservation procedure, this duplication of the blood pressure curve can be achieved by one form of the method of the invention that includes the following steps. The first step in the process is to obtain in a conventional manner a blood pressure chart recorder tracing from the patient or organ being treated. The dotted lines 63 of FIG. 11 of the drawings which is a plot of pressure versus time, illustrates a typical pulse wave-form. Using this information, the pulse rate and upstroke-rise time can be calculated and programmed into the touch-screen unit 60 in a manner well understood by those skilled in the art (see FIGS. 12 and 13). The dotted lines 65 of FIG. 11 of the drawings illustrate a stroke volume decrease, while the solid line 67 illustrates a decrease in upstroke time.

With the forgoing in mind, the basic design theory of the apparatus of the invention is that once the pulse wave and flow patterns are duplicated, pressure and flow will be controlled by the peripheral resistance of the blood vessels, there will be no variance in blood pressure/flow patterns; the capillary beds (microcirculation) will be filled and flushed with a full flow of blood; there will be normal oxygenation of all tissues; and all waste products (metabolites) will be effectively removed. In addition, the pulsatile flow created by the apparatus of the present invention has been proven to be vastly superior to non-pulsatile flow and non-physiologic "pulsatile flow" created by other types of prior art apparatus. More particularly, based on a study of 194 related articles published between 1952 and 2006, it has been determined that pulsatile flow decreased the incidence of post-operative deaths in pediatric and adult patients, significantly improved blood flow of vital organs including brain, heart, liver, and pancreas, reduced systemic inflammatory response syndrome, significantly improved vital organ recovery in several types of animal models when compared to non-pulsatile perfusion and generates more hemodynamic energy, which better maintains the microcirculation compared with non-pulsatile flow. It has also been determined that infants receiving pulsatile blood flow during bypass surgery awakened more quickly, were more alert and required less post-operative ventilation.

In order to ready the apparatus of the invention to permit accomplishment of the method of the invention, the various components of the apparatus are assembled together in a manner illustrated in FIG. 2 of the drawings. In this regard, the hydraulic actuating unit 24 is first assembled in the manner indicated in FIG. 8 of the drawings by operably interconnecting the housing 26 with the actuator base 70 using the threaded connector ring 72. Actuator base 70 houses the previously mentioned diaphragm 42 which is interconnected with an operating shaft 74 that is reciprocally movable within base 70 in the manner indicated by the arrow 75 of FIG. 8. Next, the assembled actuating unit 24 is mounted within a capture plate 78 that is interconnected with vertical support member 22b in the manner shown in FIG. 2 of the drawings. This done, the fluid reservoir or chamber 28 of the actuating unit, is filled with a suitable pressure transmissive fluid.

With the actuating unit 24 properly mounted on the support structure in the manner shown in FIG. 2, the pulsatile flow pump 30 is interconnected with the actuating unit so that the inlet 30a of the mechanism is in fluid communication with outlet 28a of the actuating unit and is in fluid communication with the fluid reservoir or chamber 28 of the actuating unit.

Figure 10:
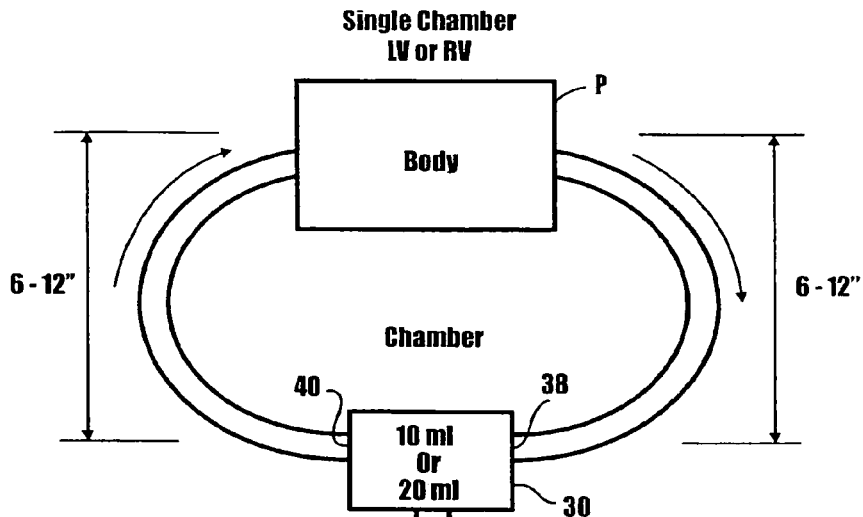
FIG. 10 is a generally diagrammatic view illustrating the manner of interconnection of the hydraulic actuator sub-assembly and the pulsatile pump sub-assembly with the patient.

As previously mentioned and as indicated in FIGS. 2 and 9 of the drawings, the compressible-expandable bladder 36 of the pulsatile flow pump is centrally disposed within chamber 34 of housing 32 so that the receiving and delivery ports 38 and 40 thereof extend outwardly from housing 32 to enable them to be interconnected with the patient in the manner illustrated in FIG. 10.

Figure 12:
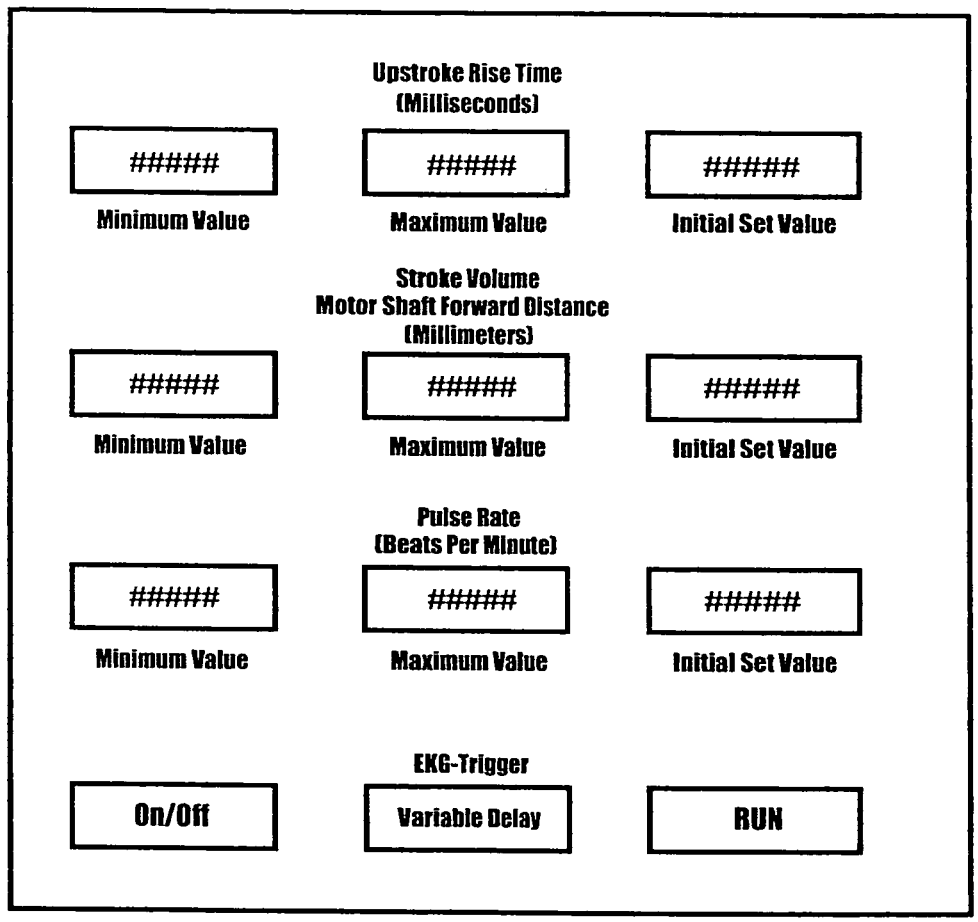
FIG. 12 is a generally diagrammatic view illustrating one type of image that appears on the touch-screen sub-assembly of the apparatus.
Figure 13:
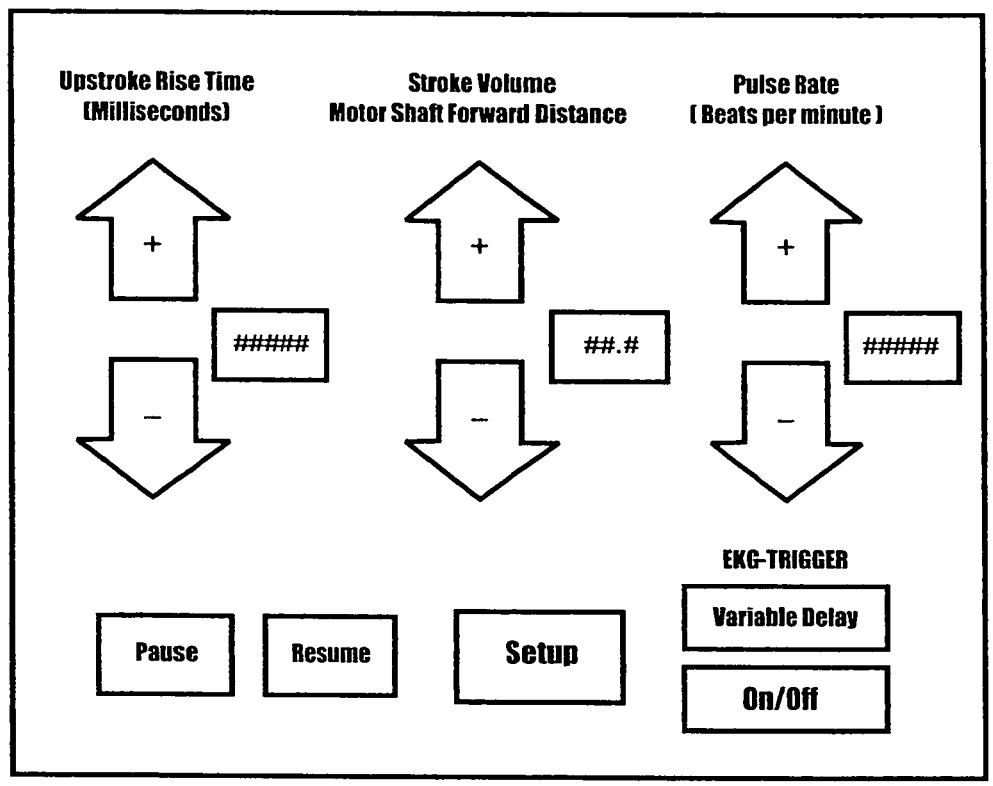
FIG. 13 is a generally diagrammatic view illustrating another type of image that appears on the touch-screen sub-assembly of the apparatus.

Following the programming of the motion controller and the touch-screen unit in a manner well understood by those skilled in the art, the pumping or perfusion step is commenced by manipulating the stroke volume control image appearing on the touch-screen in a manner such that the blood pressure curve matches the chart recorder blood pressure reading obtained from the patient (see for example, FIGS. 12 and 13). Other applications, such as ventricular assist (LVAD, RVAD, BiVAD), ECMO, etc., may have different perfusion requirements and the system of the present invention is uniquely able to adapt to each application.

As previously mentioned, the pumping or perfusion step is accomplished by the cooperative interaction of the hydraulic actuator sub-assembly 24 and the pulsatile flow pump 30 of the invention. In this regard as illustrated in FIG. 8, the hydraulic actuator sub-assembly 24 includes a reciprocating shaft 74 that is interconnected with diaphragm 42 at one extremity 74a and has, at its other extremity 72b, an enlarged diameter head portion 74c that is acted upon by shaft 48 of the voice control motor 46 as the motor shaft reciprocates under the control of the motion controller 50.

As shaft 74 of the actuator sub-assembly 24 reciprocates, diaphragm 42 acts upon a pressure transmissive fluid contained within the actuator chamber 28 in a manner to generate a pulsatile pressure on the transmissive fluid. The pulsatile pressure generated on the transmissive fluid in turn results in a pulsatile pressure being exerted on bladder 36 in a manner to controllably vary the volume thereof. More particularly, as the bladder 36 is collapsed by the pressure exerted on the bladder by the pressure transmissive fluid, blood is forced outwardly of the delivery port 40 of the bladder 36 and through the novel tricuspid valve 36c that is mounted within the delivery port (FIG. 9). Conversely, a reduction in pressure of the transmissive fluid caused by a retraction of the reciprocating shaft 48 permits the compressible-expandable bladder 36 to expand in a manner to allow highly desirable positive pressure/passive infilling via the inflow or receiving port 38 via the tricuspid valve 36b that is mounted within the port (see FIGS. 9 and 10).

Tricuspid valves 36b and 36c, which are held in position by threaded connectors 37, uniquely mimic the shape and action of the native tricuspid heart valve which is located on the right side of the heart between the right atrium and the right ventricle. During normal operation of the heart, the right atrium receives deoxygenated blood from the superior and inferior vena cavae and the coronary sinus and pumps it into the right ventricle through the heart's tricuspid valve.

Continued operation of the pulsatile flow pump 30, the hydraulic actuator sub-assembly 24 and voice-coil motor 46, which is under the control of the motion controller 50, will generate a physiologic pulsatile blood flow that very accurately duplicates blood pressure and flow patterns of the patient while handling the patient's blood gently.

When the apparatus of the invention is used to partially support a beating heart in carrying out procedures such as ventricular assist and Extracorporeal Membrane Oxygenation (ECMO), the proper timing of each beat of the pump is vital. In this regard, medical research has shown that a pump system that is assisting a beating heart needs to trigger shortly after the actual heart beat. Pumping at the same time actually puts an additional load on the heart. The variable delay allows the exact desired time interval to be set which gives optimal healing. Each beat shows two pressure peaks on the monitor.

Figure 14:
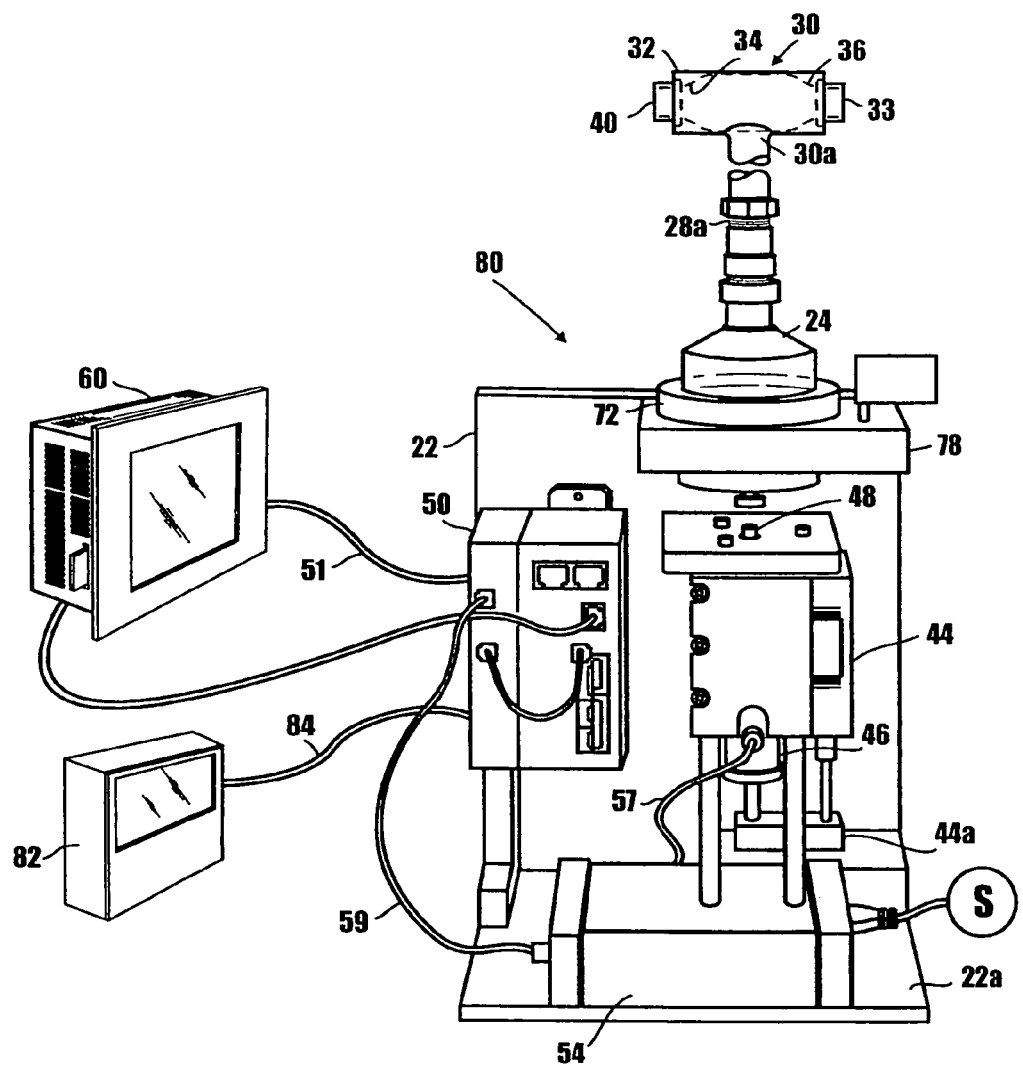
FIG. 14 is a generally perspective view of an alternate form of physiological pulsatile pump system of the present invention.

In accomplishing the procedures identified in the preceding paragraph, an alternate form of the apparatus of the invention is used. This alternate form of the apparatus of the invention, which is illustrated in FIG. 14 of the drawings and is generally designated by the numeral 80, uniquely includes an EKG-trigger circuit. This alternate form of the apparatus is similar in most respects to that illustrated in FIGS. 2 through 13 and like numerals are used in FIG. 14 to identify like components. In the apparatus of this latest form of the invention, an EKG unit 82 is interconnected with the motion controller 50 by means of a suitable cable 84. With this construction, during the accomplishment of the operational procedure, the system can be triggered by an electronic EKG signal obtained from the patient's heart so that that the mechanism 30 beats every time the patient's heart beats. In some laboratory studies, when a heart was removed and placed on an oxygen preservation perfusion machine, the heart continued to beat out of the body (ex vivo). That application would also require an EKG-trigger with a variable delay. In this alternate form of the apparatus, when the EKG-trigger is activated, the trigger uniquely overrides the pulse rate control on the touch-screen 60 (see FIG. 13). In the present invention, the EKG-trigger and variable delay are built-in to the electronics, and are controlled on the touch-screen with read-outs. In the prior art system, the EKG unit was a later "add-on" and thus was an additional external circuit which acted as a relay between patient and the pump system. In the prior art unit there were more cords, no read-out of the delay and the unit could only be activated by flipping a switch on the back of the pump as compared to an automatic override on the new system.

Figure 15:
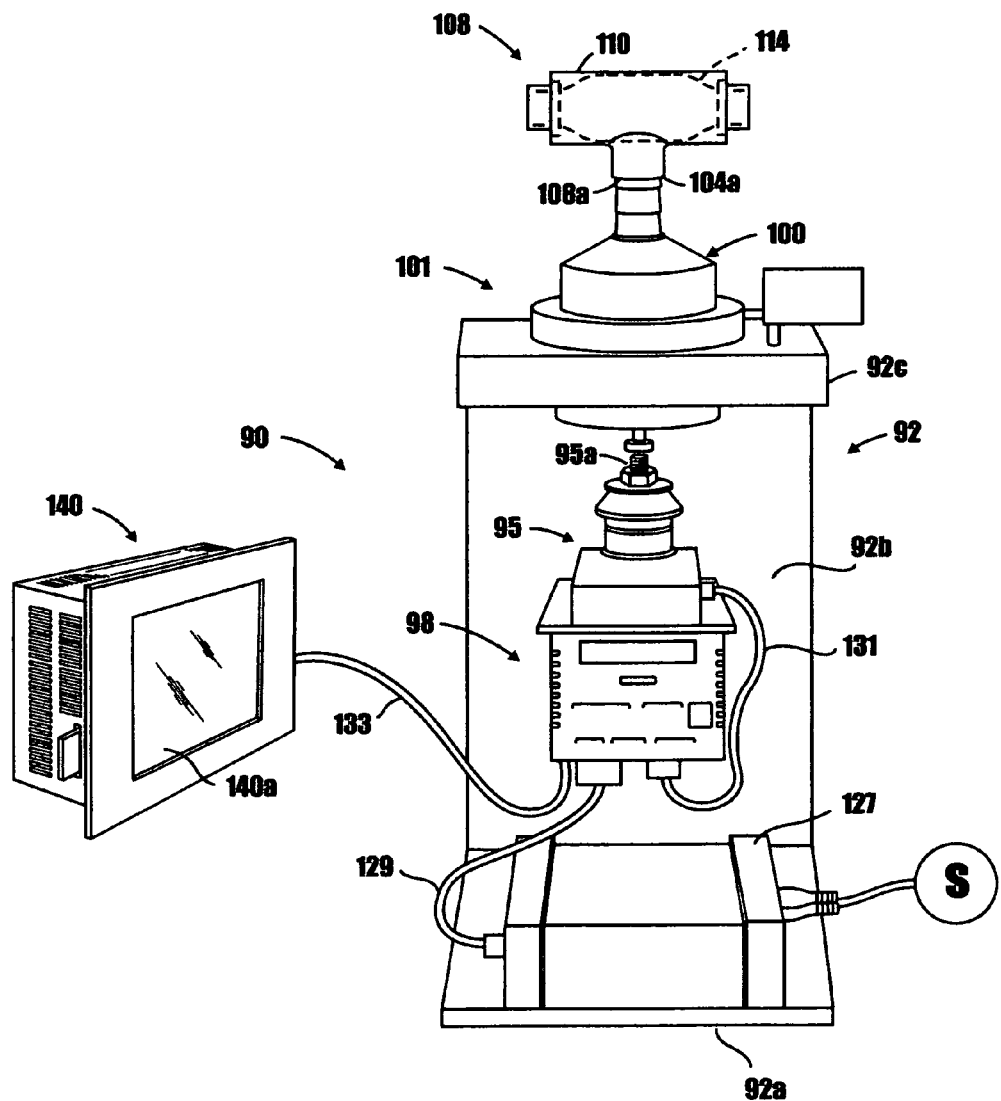
FIG. 15 is a generally perspective view of still another form of physiological pulsatile pump system of the present invention.
Figure 16:
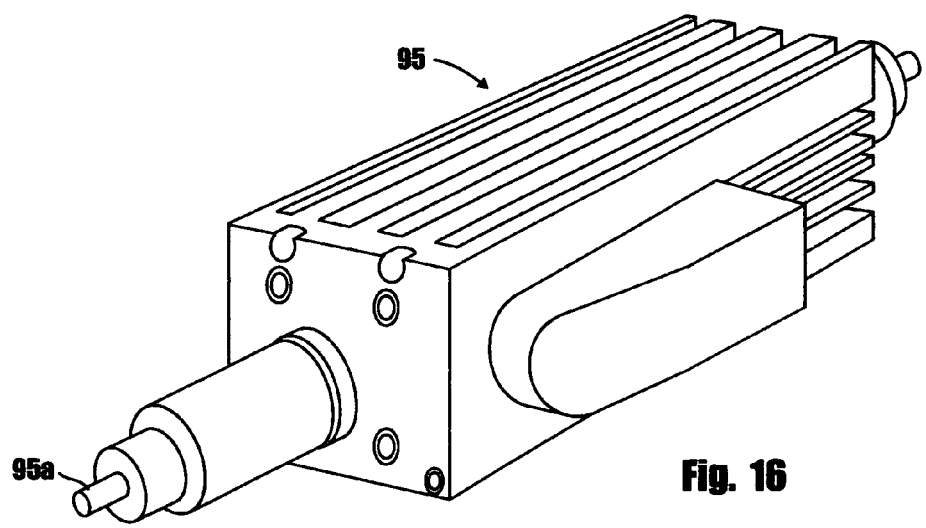
FIG. 16 is a generally perspective view of the motor of the assembly shown in FIG. 15.

Referring now to FIG. 15 the drawings, still another form of the physiologic pulsatile pump apparatus of the present invention is there illustrated and generally designated by the numeral 90. This latest form of the apparatus is also similar in many respects to that illustrated in FIGS. 2 through 13 and like numerals are used in FIG. 15 to identify like components. Apparatus 90, which is also adapted primarily for use in cardiopulmonary bypass, ventricular assist (LVAD, RVAD, BiVAD), ECMO, organ preservation, fetal cardiac bypass, cancer treatment, and various areas of circulation research, here comprises a support assembly 92 having a base member 92*a* and a substantially vertical member 92*b* that is connected to the base member and extends therefrom. The actuator motor system 95 of this latest form of the invention, which is attached to member 92*b* in the manner shown in FIG. 15, is of a different construction from the voice-coil actuator motor of the previously described embodiments. More particularly, the voice-coil system of the previously described embodiments is a non-communicating system that comprises a motor that includes a piston, or shaft, that moves back and forth through a dedicated stroke. In sharp contradistinction, the actuator motor system 95 of this latest form of the invention, the construction of which is illustrated in FIG. 16, comprises a servo system, which advantageously is a fully communicating system. In the present form of the invention, motor system 95 is manufactured by Copley Controls of Canton, Mass. and is sold under the designation "STA 2504". In using this motor system, constant monitoring of the position and velocity of the piston 95*a* is possible, thereby permitting more accurate control for superior results. The details of the construction and operation of this novel motor system are available from Copley Controls. In a manner presently to be described, during operation of the apparatus, piston or shaft 95*a* controllably acts upon the actuator member of the apparatus to create the pulsating flow.

Operably associated with and adapted to control motor system 95 is a motion controller system 98 that is also available from Copley Controls. This novel controller system, which is sold under the name and style "XENUS Micro", is a compact, AC power servo drive for continuously monitoring and controlling the movement of the shaft 95*a* of the actuator motor system. More particularly, motion controller system 98, which is mounted on motor system 95 (see FIG. 15), continuously monitors and controls the position, velocity, and torque of the shaft of the motor system. The details of the construction and operation of this novel controller system are available from Copley Controls. Motor system 95 and controller system 98, along with a hydraulic actuating sub-assembly 100, the character of which will presently be described, comprise the actuator system 101 of the invention that operates the important pulsatile flow pump of this latest form of the invention.

Figure 17:
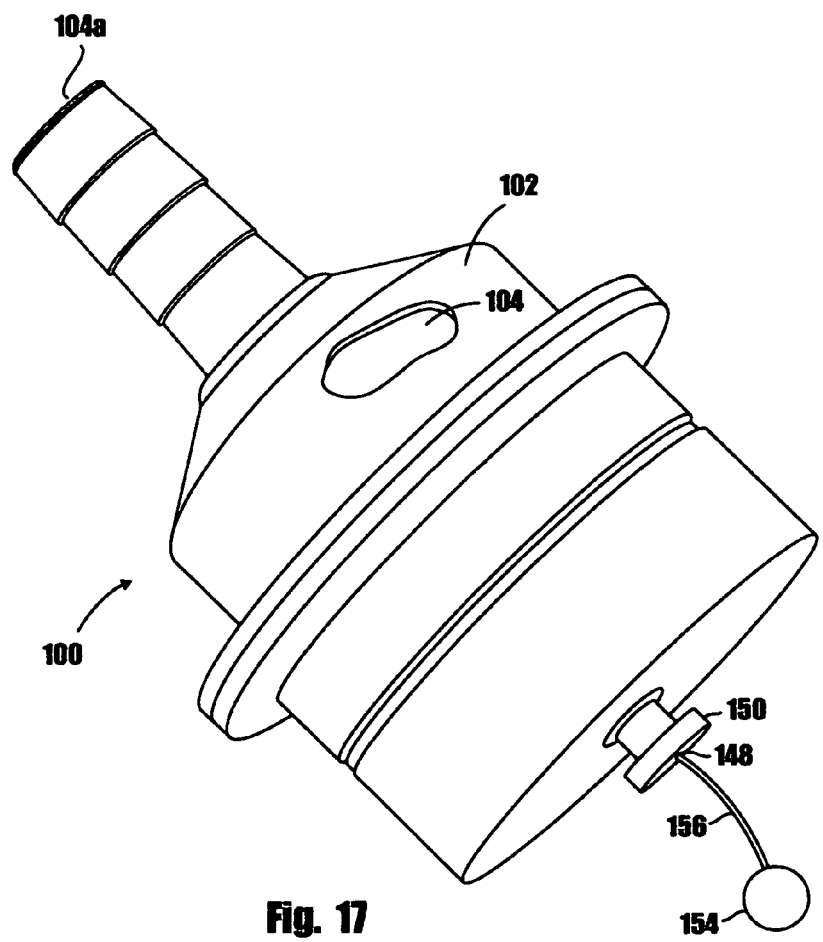
FIG. 17 is a generally perspective view of the hydraulic actuator sub-assembly of the apparatus shown in FIG. 15.

The hydraulic actuating sub-assembly 100, which is of a somewhat different construction from the previously described hydraulic actuator sub-assembly 24, is connected to a horizontal support member 92*c* that is connected to the vertical member 92*b* in the manner shown in FIG. 15 of the drawings. As best seen in FIG. 17, hydraulic actuator sub-assembly 100 includes a housing 102 that defines a fluid chamber 104 having an outlet 104*a*. The function of this alternate form of hydraulic actuating sub-assembly will presently be described.

Operably associated with the hydraulic actuating sub-assembly 100 is the important pulsatile flow pump 108 of this latest form of the invention, which is also of a slightly different construction from that earlier described. As indicated in FIG. 19 of the drawings, pump 108 includes a fluid inlet port 108*a* that is in communication with outlet 104*a* of the hydraulic actuating sub-assembly in the manner shown in FIG. 15. As will be presently described in greater detail, pulsatile flow pump 108 in cooperation with the actuating sub-assembly 100, functions to generate a pulsatile blood flow that substantially duplicates that of the patient as recorded by a chart recorder.

As best seen by referring to FIGS. 15 and 19, pump 108 comprises a housing 110 defining a chamber 112 within which is mounted a disposable, compressible-expandable bladder 114 formed from a carbothane thermoplastic elastomer. This material is highly advantageous for the present application because it does not cause blood damage (hemolysis) and exhibits good biocompatible and mechanical properties. Bladder 114 includes a bladder chamber 114*a* having a receiving port 118 and a delivery port 120, both of which are in communication with the patient "P" in the manner illustrated in FIG. 20. As indicated in FIG. 19 of the drawings, the surfaces of the bladder are coated with a proprietary coating "C" that is produced by AllvivoVascular, Inc. of Lake Forest, Calif. This coating material, the details of which are available from AllvivoVascular, Inc., uniquely protects against thrombus and significantly reduces systematic inflammatory response which occurs in about 1% of pediatric heart patients.

Figure 18:
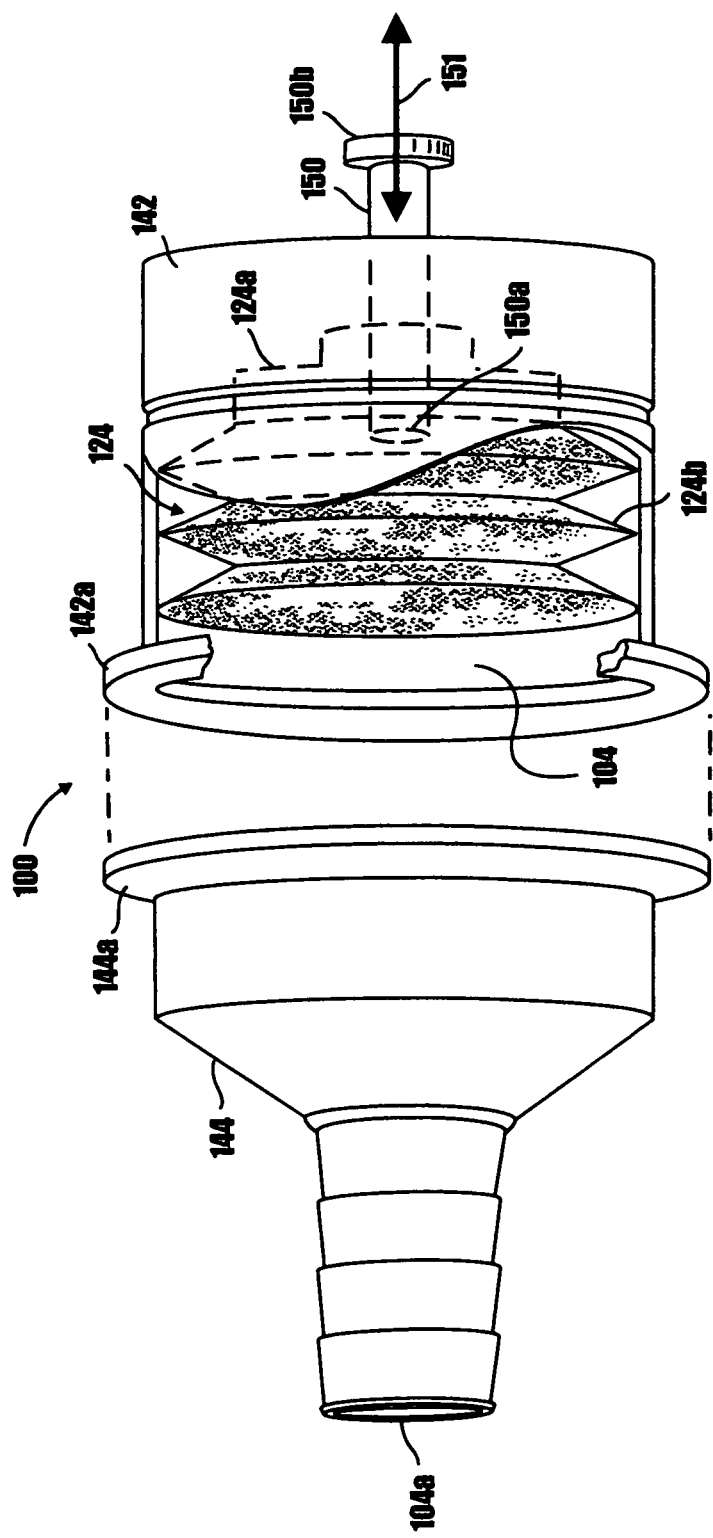
FIG. 18 is a generally perspective, exploded view of the hydraulic actuator sub-assembly shown in FIG. 17.

As best seen in FIG. 18 of the drawings, sealably mounted within the fluid actuator chamber 104 of the hydraulic actuator sub-assembly 100 is a bellows type actuating member or diaphragm 124 which, during operation of the apparatus, acts upon a pressure transmissive fluid contained within the actuator chamber 104 in a manner to generate a pulsatile pressure on the transmissive fluid. Diaphragm 124, which is of a unique construction having a base 124*a* and a bellows-like side wall 124*b*, is commercially available from the Vi-Cas Mfg Company of Cincinnati, Ohio. As will be described in greater detail hereinafter, the pulsatile pressure generated on the transmissive fluid by the actuating member 124 results in a pulsatile pressure being exerted on bladder 114 in a manner to controllably vary the volume thereof.

As previously discussed, motor system 95, which is operably associated with hydraulic actuator sub-assembly 114, functions to controllably move the actuating member 124 of the hydraulic actuating sub-assembly within the fluid chamber 104 thereof (see FIG. 18).

As illustrated in FIG. 15 of the drawings, to provide electrical power to the motor system 95 and the controller system 98, a conventional power supply 127 is suitably mounted on the horizontal member 92*a* of the support assembly 92 and is connected to a suitable source of power "S". Power supply 127 is readily commercially available from a number of sources, including the previously identified H2W Technologies of Valencia, Calif. Suitable cabling, including cables 129 and 131, interconnect the power supply with the motor system 95 and the controller system 98.

Operably associated with the controller system 98 via a connector 133 is a touch-screen unit 140 (FIG. 15). Touch-screen unit 140, which forms a part of the actuator system 101, includes desired color read-outs, is readily commercially available from a number of sources including the ESA Technology Company of Windsor, Calif. Touch-screen unit 140 here comprises a state-of-the-art touch-terminal that greatly simplifies the operation and control of the interactive components of the apparatus of the present invention. The touch-screen unit includes a rugged touch-screen 140a upon which graphic images in various formats can be imported. During operation of the apparatus of the invention, the read-outs on the touch-screen that are easy to see can be quickly and precisely changed on-the-fly and, in a manner presently to be discussed, automatically activate with an EKG signal.

As in the earlier described embodiments, the apparatus of this latest form of the invention is designed to accurately duplicate a blood pressure curve by independently varying pulse rate, that is the number of beats per minute; stroke volume, that is the volume of blood pumped on each beat; and upstroke-rise time, that is the duration of time from the start to peak pressure at the top of the curve on each beat. In a potential clinical application as, for example, a cardiopulmonary bypass procedure or an organ preservation procedure, this duplication of the blood pressure curve can be achieved by one form of the method of the invention that includes the following steps. The first step in the process is to obtain, in a conventional manner, a blood pressure chart recorder tracing from the patient or organ being treated. The dotted lines 63 of FIG. 11 of the drawings, which is a plot of pressure versus time, illustrate a typical pulse wave-form. Using this information, the pulse rate and upstroke-rise time can be calculated and programmed into a touch-screen unit such as unit 140 (FIG. 15) in a manner well understood by those skilled in the art (see FIGS. 12 and 13). The dotted lines 65 of FIG. 11 of the drawings illustrate a stroke volume decrease, while the solid line 67 illustrates a decrease in upstroke time.

With the forgoing in mind, the basic design theory of the apparatus of the invention is that once the pulse wave and flow patterns are duplicated, pressure and flow will be controlled by the peripheral resistance of the blood vessels, there will be no variance in blood pressure/flow patterns; the capillary beds (microcirculation) will be filled and flushed with a full flow of blood; there will be normal oxygenation of all tissues; and all waste products (metabolites) will be effectively removed.

Figure 20:
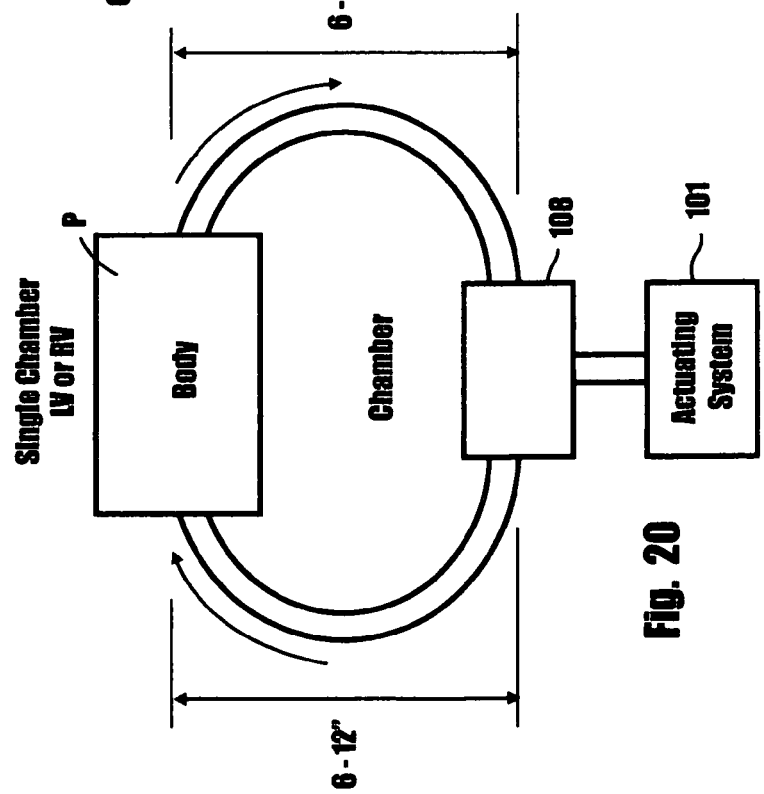
FIG. 20 is a generally diagrammatic view illustrating the manner of interconnection of the hydraulic actuator sub-assembly and one form of the pulsatile pump sub-assembly with the patient.

In order to ready the apparatus of this latest form of the invention to permit accomplishment of one form of the method of the invention, the various components of the apparatus are assembled together into the configuration illustrated in FIGS. 15 and 20 of the drawings. In this regard, the hydraulic actuating sub-assembly 100 is first assembled in the manner indicated in FIG. 17 of the drawings so that the bellows type actuating member or diaphragm 124 is properly secured within base portion 142. With the bellows type actuating member in position within base portion 142 and with the operating shaft 95a of the motor system properly interconnected with the actuating member 124, the flange portion 142a of the base portion 142 is sealably connected to the flange portion 144a of the top portion 144 by any suitable means such as, by way of example, adhesive bonding.

Following its assembly, the actuating sub-system 100 is connected to horizontal support member 92c in the manner shown in FIG. 15 of the drawings. Next, the pulsatile flow pump 108 is interconnected with the system so that the inlet 108a of the pump is in fluid communication with outlet 104a of the actuating sub-system. With the pulsatile flow pump 108 interconnected with the system in the manner shown in FIG. 15, the fluid reservoir, or chamber 104 of the actuating sub-system, as well as the bladder chamber 114a of the bladder 114 of the pulsatile flow pump 108, is filled with a suitable pressure transmissive fluid via a fill port 148 (FIG. 17), fill port 148 provided in an operating shaft 150 that is reciprocally movable within base 70 in the manner indicated by the arrow 151 of FIG. 18. As illustrated in FIG. 17, fill port 148 is connected with a source of transmissive fluid 154 via a fill line 156.

As previously mentioned, and as indicated in FIG. 19 of the drawings, the compressible-expandable bladder 114 of the pulsatile flow pump is centrally disposed within chamber 112 of housing 110 so that the receiving and delivery ports 118 and 120 thereof extend outwardly from housing 110 to enable them to be interconnected with the patient in the manner illustrated in FIG. 20.

Following the programming of the motion controller and the touch-screen unit in a manner well understood by those skilled in the art, the pumping or perfusion step is commenced by manipulating the stroke volume control image appearing on the touch-screen in a manner such that the blood pressure curve matches the chart recorder blood pressure reading obtained from the patient (see for example, FIGS. 12 and 13). Other applications such as ventricular assist (LVAD, RVAD, BiVAD), ECMO, etc., may have different perfusion requirements and the system of the present invention is uniquely able to adapt to each application.

As previously mentioned, the pumping or perfusion step is accomplished by the cooperative interaction of the pulsatile flow pump 108 and the actuator system 101 of the invention and more particularly by the hydraulic actuating sub-assembly 100 of the actuator system 101. In this regard, diaphragm 124 is acted upon by reciprocating operating shaft 150 which is interconnected with diaphragm 124 at extremity 150a thereof. At its other extremity 150b, operating shaft 150 is acted upon by shaft 95a of motor 95 as the motor shaft reciprocates under the control of the motion controller 98.

As the operating shaft 150 of the actuating system reciprocates, diaphragm 124 acts upon a pressure transmissive fluid contained within the actuator chamber in a manner to generate a pulsatile pressure on the transmissive fluid. The pulsatile pressure generated on the transmissive fluid in turn results in a pulsatile pressure being exerted on bladder 114 in a manner to controllably vary the volume thereof. More particularly, as the bladder 114 is collapsed by the pressure exerted on the bladder by the pressure transmissive fluid, blood is forced outwardly of the delivery port 120 of the bladder and through the novel tricuspid valve 156 that is mounted within the delivery port (FIG. 19). Conversely, a reduction in pressure of the transmissive fluid caused by a retraction of the reciprocating shaft 150 permits the compressible-expandable bladder 114 to expand in a manner to allow highly desirable positive pressure/passive infilling via the inflow or receiving port 118 via the tricuspid valve 154 that is mounted within the port (see FIG. 19).

As in the earlier described embodiments of the invention, tricuspid valves 154 and 156 which are held in position by threaded connectors 157 uniquely mimic the shape and action of the native tricuspid heart valve which is located on the right side of the heart between the right atrium and the right ventricle. During normal operation of the heart, the right atrium receives deoxygenated blood from the superior and inferior vena cavae and the coronary sinus and pumps it into the right ventricle through the heart's tricuspid valve. As indicated in FIG. 19, both of the tricuspid valves 154 and 156 as well as both of the threaded connectors 157, are coated with proprietary coating "C".

Continued operation of the pulsatile flow pump 108, the hydraulic actuating sub-assembly 100, and motor system 95 which is under the control of the controller system 98, will generate a physiologic pulsatile blood flow that very accurately duplicates blood pressure and flow patterns of the patient while handling the patient's blood gently.

As previously mentioned, when the apparatus of the invention is used to partially support a beating heart in carrying out procedures such as ventricular assist and Extracorporeal Membrane Oxygenation (ECMO), the proper timing of each beat of the pump is vital. In this regard, medical research has shown that a pump system that is assisting a beating heart needs to trigger shortly after the actual heart beat. Pumping at the same time actually puts an additional load on the heart. The variable delay allows the exact desired time interval to be set which gives optimal healing. Each beat shows two pressure peaks on the monitor.

Figure 21:
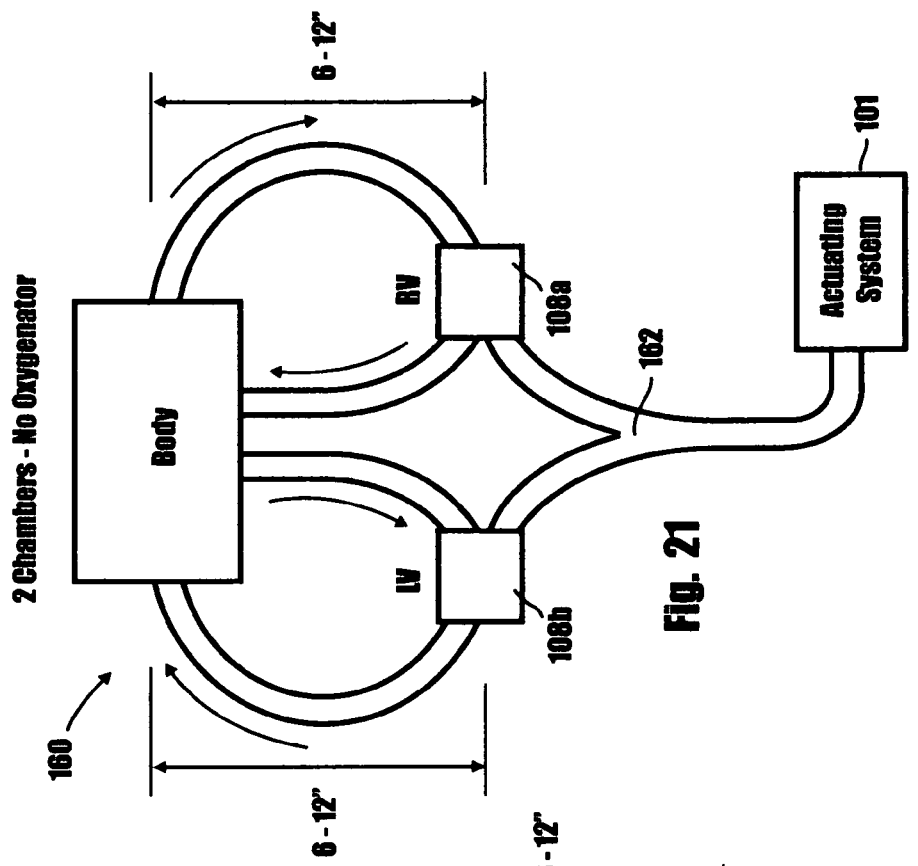
FIG. 21 is a generally diagrammatic view illustrating the manner of interconnection of the hydraulic actuator sub-assembly and another form of the pulsatile pump sub-assembly with the patient.

Turning now to FIG. 21 of the drawings, still another form of the apparatus of the invention is there illustrated and generally designated by the numeral 160. This apparatus is similar in most respects to the apparatus described in the preceding paragraphs and designated in the drawings by the numeral 90. As indicated in FIG. 21, the apparatus of this latest form of the invention comprises first and second substantially identical pulsatile flow pumps 108a and 108b that are interconnected via a "Y" connector 162 with actuator system 101 that is substantially identical in construction and operation to that previously described. Pulsatile flow pumps 108a and 108b have a volume of between about 1 ml and about 100 ml.

In operating this latest form of the invention, the actuator system 101 which includes the hydraulic actuating sub-assembly 100, simultaneously actuates pulsatile flow pumps 108a and 108b in the same manner as a healthy heart. This novel two-chamber pumping system provides physiologic flows and pressures to both the systemic and pulmonary circulations, even though the pressure in the lungs is about ⅕ of the systemic circulation. Uniquely, this novel two-chamber pumping system greatly affects mortality and morbidity patient outcomes.

Figure 22:
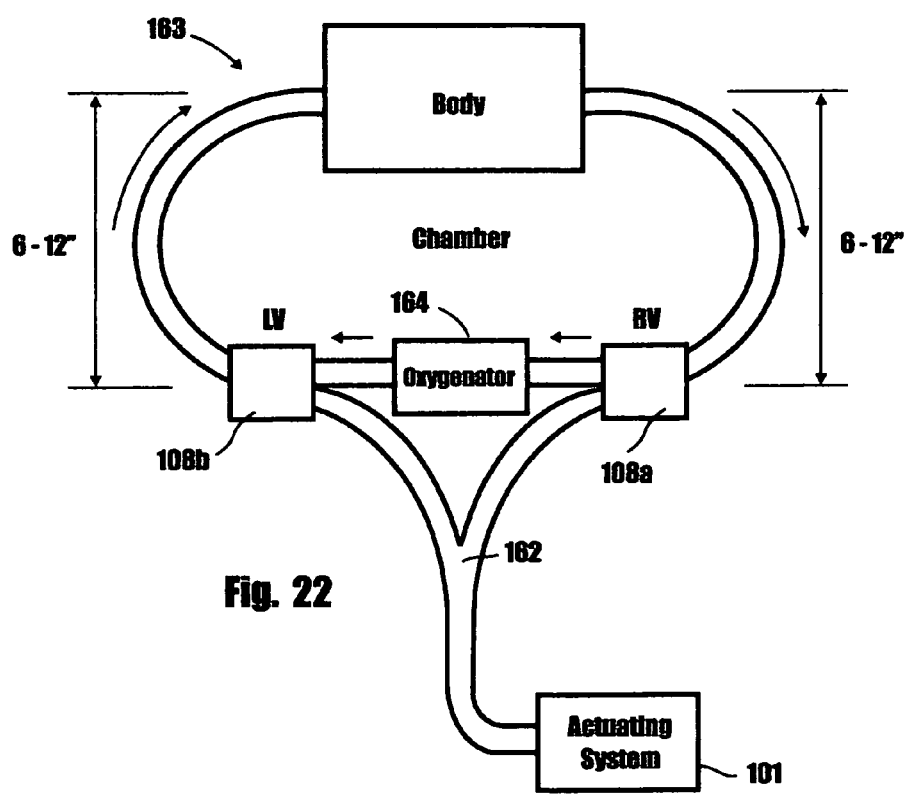
FIG. 22 is a generally diagrammatic view illustrating the manner of interconnection of the actuating system of the invention with still another form of the pulsatile pump sub-assembly with the patient

Referring finally to FIG. 22 of the drawings, yet another form of the apparatus of the invention is there illustrated and generally designated by the numeral 163. This apparatus is similar in most respects to the previously described apparatus 160 and like numerals are used in FIG. 22 to identify like components. As indicated in FIG. 22, the apparatus of this latest form of the invention also comprises first and second substantially identical pulsatile flow pumps 108a and 108b, each having a volume of between about 1 ml and about 100 ml. Pulsatile flow pumps 108a and 108b are interconnected with actuator system 101 via a "Y" connector 162 to provide a system that is substantially identical in construction and operation to that previously described. However, in the manner shown in FIG. 22, in this latest form of the invention a conventional oxygenator 164 is disposed between and interconnected with the first and second pulsatile flow pumps 108a and 108b. Accordingly, pump 108a functions as a pre-oxygenator and pump 108b functions as a post-oxygenator. While oxygenator 164 is commercially available from various sources, an oxygenator offered for sale by the Dideco Company of Arvada, Colo. has proven satisfactory for use in the apparatus of FIG. 22.

As was the case in operating the form of the invention shown in FIG. 21 of the drawings, in operating this latest form of the invention, the actuator system 101 which includes the hydraulic actuating sub-assembly 100, simultaneously actuates pulsatile flow pumps 108a and 108b in the same manner as a healthy heart and the oxygenator functions to exchange oxygen and carbon dioxide in the blood of the patient during the surgical procedure.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

The invention claimed is:

1. A physiologic pulsatile pump apparatus comprising:
   (A) first and second operably interconnected pulsatile pumps, each of said first and second pulsatile pump comprising:
      (i) a housing defining a chamber having an inlet port; and
      (ii) a compressible-expandable bladder sealably mounted within said housing, said bladder having a receiving port and a delivery port; and
   (B) an actuator system connected to said first and second pulsatile pumps for operating said pumps, said actuator system comprising:
      (iii) a hydraulic actuating sub-assembly comprising:
         a. a fluid chamber containing a pressure transmissive fluid, said fluid chamber having an outlet port in communication with said inlet port of said housing; and
         b. an actuating member mounted within said fluid chamber for movement within said fluid chamber in a manner to generate a pulsatile pressure on said transmissive fluid so as to cause a pulsatile pressure on said bladder to vary the volume thereof; and
      (vi) a motor operably associated with said hydraulic actuating sub-assembly for controllably moving said actuating member thereof within said fluid chamber.

2. The apparatus as defined in claim 1, further including a motion controller operably associated with said motor for controlling said motor.

3. The apparatus as defined in claim 1, further including a tricuspid valve mounted within said delivery port of said bladder of each of said first and second pulsatile pumps and a tricuspid valve mounted within said receiving port of said bladder of each of said first and second pulsatile pumps.

4. The apparatus as defined in claim 1, wherein said bladder of each of said first and second pulsatile pumps is coated with a coating material that protects against thrombus.

5. The apparatus as defined in claim 1, wherein said motor includes a reciprocally movable shaft in communication with said actuating member of said hydraulic actuator for imparting movement thereto.

6. The apparatus as defined in claim 1, wherein said actuating member of said hydraulic actuating sub-assembly is coated with a coating material that protects against thrombus.

7. The apparatus is defined in claim 1, further including a support assembly having a base member and a substantially vertical member connected to said base member and extending there from, said motor being interconnected with said vertical member.

8. The apparatus as defined in claim 1, further including a touch-screen operably associated with said motion controller for controlling said motion controller.

9. The apparatus as defined in claim 1, further including an oxygenator disposed between and interconnected with said first and second operably interconnected pulsatile pumps.

10. An apparatus for use in the cardiopulmonary bypass, ventricular assist (LVAD, RVAD, BiVAD), ECMO, organ preservation, fetal cardiac bypass, cancer treatment, and various areas of circulation research comprising:
    (A) a pulsatile pump comprising:
       (i) a housing defining a chamber having an inlet port; and (ii) a disposable, compressible-expandable bladder sealably mounted within said housing, said bladder having a receiving port and a delivery port; and (B) an actuator system connected to said pulsatile pump for operating said pump, said actuator system comprising:

(iii) a support assembly having a base member and a substantially vertical member connected to said base member and extending there from;

(iv) a hydraulic actuating sub-assembly connected to said vertical member of said support, said hydraulic actuator sub-assembly comprising a fluid chamber having an outlet and an actuating member movable within said fluid chamber;

(v) an actuator motor system including a shaft operably associated with said actuating member of said hydraulic actuating sub-assembly for moving said actuating member within said fluid chamber;

(vi) a motion controller operably associated with said actuator motor system for continuously monitoring and controlling the movement of said shaft of said actuator motor system for controlling movement thereof; and (vii) a touch-screen operably associated with said motion controller for controlling said motion controller.

11. The apparatus as defined in claim 10, further including a tricuspid valve mounted within each of said receiving and delivery ports of said bladder of said pulsatile pump.

12. The apparatus as defined in claim 10, wherein said bladder of said first pulsatile pump is coated with a coating material that protects against thrombus.

13. The apparatus as defined in claim 10, wherein said actuating member of said hydraulic actuating sub-assembly is coated with a coating material that protects against thrombus.

14. An apparatus for use in the cardiopulmonary bypass, ventricular assist (LVAD, RVAD, BiVAD), ECMO, organ preservation, fetal cardiac bypass, cancer treatment, and various areas of circulation research comprising:

(A) a first pulsatile pump comprising:
(i) a generally cylindrically shaped housing defining a chamber having an inlet port and an output port;
(ii) a disposable, compressible-expandable bladder sealably mounted within said housing, said bladder having a receiving port, a delivery port and a coating that protects against thrombus;
(iii) a tricuspid valve mounted within said receiving port of said bladder; and
(iv) a tricuspid valve mounted within said delivery port of said bladder; and (B) an actuator system connected to said pulsatile pump for operating said pump, said actuator system comprising:
(v) a support assembly having a base member and a substantially vertical member connected to said base member and extending there from;
(vi) a hydraulic actuating sub-assembly connected to said vertical member of said support, said hydraulic actuator sub-assembly comprising a fluid chamber having an outlet and an actuating member movable within said fluid chamber;
(vii) an actuator motor system including a shaft operably associated with said actuating member of said hydraulic actuating sub-assembly for moving said actuating member within said fluid chamber;
(viii) a motion controller operably associated with said actuator motor system for continuously monitoring and controlling the movement of said shaft of said actuator motor system for controlling movement thereof;
(ix) a touch-screen operably associated with said motion controller for controlling said motion controller; and
(x) a power supply operably interconnected with said actuator motor system, said motion controller and said touch screen.

15. The apparatus as defined in claim 14 in which said actuating member of said hydraulic actuating sub-assembly is coated with a coating material that protects against thrombus.

16. The apparatus as defined in claim 14 further including a second pulsatile pump operably associated with said first pulsatile pump, said second pulsatile Pump comprising:
(C) a generally cylindrically shaped housing defining a chamber having an inlet port and an output port;
(D) a disposable, compressible-expandable bladder sealably mounted within said housing, said bladder having a receiving port, a delivery port and a coating that protects against thrombus;
(E) a tricuspid valve mounted within said receiving port of said bladder; and
(F) a tricuspid valve mounted within said delivery port of said bladder.

17. The apparatus as defined in claim 16, wherein said first and second pulsatile pumps have a volume of between about 1 ml and about 100 ml.

18. The apparatus as defined in claim 16, further including an oxygenator disposed between and operably associated with said first and second pulsatile pumps.

* * * * *